US010311462B2

(12) United States Patent
Lindstrom, Jr. et al.

(10) Patent No.: US 10,311,462 B2
(45) Date of Patent: Jun. 4, 2019

(54) MUSIC STREAMING FOR ATHLETIC ACTIVITIES

(71) Applicant: NIKE, Inc., Beaverton, OR (US)

(72) Inventors: Harold L. Lindstrom, Jr., Portland, OR (US); Willoughby H. Walling, Portland, OR (US); Christopher L. Andon, Portland, OR (US)

(73) Assignee: NIKE, Inc., Beaverton, OR (US)

( * ) Notice: Subject to any disclaimer, the term of this patent is extended or adjusted under 35 U.S.C. 154(b) by 188 days.

(21) Appl. No.: 14/723,670

(22) Filed: May 28, 2015

(65) Prior Publication Data

US 2016/0346604 A1    Dec. 1, 2016

(51) Int. Cl.
| | |
|---|---|
| *A61B 5/00* | (2006.01) |
| *A61B 5/11* | (2006.01) |
| *G06F 17/30* | (2006.01) |
| *G06Q 30/02* | (2012.01) |
| *G06F 1/16* | (2006.01) |
| *A61B 5/024* | (2006.01) |
| *G06F 19/00* | (2018.01) |

(52) U.S. Cl.
CPC ........ *G06Q 30/0241* (2013.01); *A61B 5/1118* (2013.01); *A61B 5/486* (2013.01); *G06F 17/30749* (2013.01); *A61B 5/0022* (2013.01); *A61B 5/0024* (2013.01); *A61B 5/024* (2013.01); *A61B 5/1112* (2013.01); *A61B 5/6804* (2013.01); *A61B 5/6807* (2013.01); *A61B 2503/10* (2013.01); *G06F 1/163* (2013.01); *G06F 19/3481* (2013.01)

(58) Field of Classification Search
CPC ......... G06F 17/30772; G06F 17/30749; G06F 3/04842; A61B 5/024; A61B 5/1118
See application file for complete search history.

(56) References Cited

U.S. PATENT DOCUMENTS 7,824,309 B1 * 11/2010 Tadlock ............. A63B 24/0021
                                                                     482/1
8,784,116 B2    7/2014 Buck et al.
(Continued)

FOREIGN PATENT DOCUMENTS

WO    2010129252 A1    11/2010

OTHER PUBLICATIONS

Google, Android 2.2 User's Guide, May 20, 2010, Googel, Inc., pp. 1, 2, 273-281, 301-310.*

(Continued)

*Primary Examiner* — Nicholas Klicos
(74) *Attorney, Agent, or Firm* — Banner & Witcoff, Ltd.

(57) ABSTRACT

Example embodiments relate to systems, methods, apparatuses, and computer readable media relating to a user interface, that may for example, initiate transmission of a stream of audio data comprising a plurality of audio tracks from a music streaming service, and receive athletic activity data relating to a performance of an athletic activity by a user during an activity time period that includes a plurality of time intervals. For each of the plurality of time intervals, an athletic activity level is determined from the athletic activity data, a target audio track intensity corresponding to the athletic activity level is determined, and a playback of a streamed audio track corresponding to the target audio track intensity is initiated.

18 Claims, 18 Drawing Sheets

(56) References Cited

U.S. PATENT DOCUMENTS

| | | | |
|---|---|---|---|
| 9,413,710 B1* | 8/2016 | Saylor | H04L 65/403 |
| 2007/0074617 A1* | 4/2007 | Vergo | G06F 17/30743 |
| | | | 84/612 |
| 2007/0270667 A1* | 11/2007 | Coppi | A61B 5/222 |
| | | | 600/300 |
| 2008/0097633 A1* | 4/2008 | Jochelson | A63B 71/0686 |
| | | | 700/94 |
| 2008/0133441 A1* | 6/2008 | West | G06N 99/005 |
| | | | 706/46 |
| 2009/0228799 A1* | 9/2009 | Verbeeck | G06F 17/30743 |
| | | | 715/727 |
| 2010/0089221 A1* | 4/2010 | Miller | G09B 15/00 |
| | | | 84/470 R |
| 2010/0273610 A1* | 10/2010 | Johnson | A63B 24/0075 |
| | | | 482/9 |
| 2012/0028762 A1 | 2/2012 | Oleson et al. | |
| 2012/0150614 A1* | 6/2012 | Dion | G06F 17/30029 |
| | | | 705/14.32 |
| 2012/0308192 A1* | 12/2012 | Chung | H04N 21/44218 |
| | | | 386/230 |
| 2013/0228064 A1* | 9/2013 | Turner | G10H 1/40 |
| | | | 84/612 |
| 2013/0339850 A1* | 12/2013 | Hardi | G06F 3/016 |
| | | | 715/702 |
| 2014/0018046 A1 | 1/2014 | Grenier et al. | |
| 2014/0317526 A1 | 10/2014 | Hoffman | |
| 2014/0357960 A1 | 12/2014 | Phillips et al. | |
| 2015/0038806 A1 | 2/2015 | Kaleal, III et al. | |
| 2015/0289023 A1* | 10/2015 | Richman | H04N 21/2393 |
| | | | 725/32 |
| 2015/0297109 A1* | 10/2015 | Garten | A61B 5/04845 |
| | | | 600/544 |
| 2016/0189249 A1* | 6/2016 | Meyer | G06Q 30/0277 |
| | | | 705/14.66 |
| 2016/0325145 A1* | 11/2016 | Pinkerton | A63B 24/0075 |

OTHER PUBLICATIONS

Gregory Schmidt, "Wearable Gear and Apps to Make Running Healthier, and a Lot More Fun", Nov. 5, 2014, The New York Times, accessed on Sep. 13, 2017, accessed from <https://www.nytimes.com/2014/11/06/technology/personaltech/wearable-gear-and-apps-to-make-running-healthier-and-a-lot-more-fun.html>, pp. 1-3.*

Alexander George, "We Test Spotify's New Fitness Feature That Could Change How You Run", May 20, 2015, Popular Mechanics, accessed on Sep. 13, 2017, accessed from <http://www.popularmechanics.com/technology/apps/a15662/spotify-running-feature/>, pp. 1-3.*

Aug. 24, 2016—(WO) ISR & WO—App. No. PCT/US16/034047.
Nov. 23, 2018 - (EP) ESR - App. No. 16800657.5.

* cited by examiner

WORKOUT MUSIC

Fine tune your run. Set your goals, mood and music preference and get customized playlist recommendation. Sync your run when you're done and get tips and musicsuggestions to make your next run even better.

Customize Your Run Preferences

ENTER AN ARTIST OR SONG  [ ARTIST 1 ]   1100
OR
CHOOSE A STATION  [ Drop down menu ▽ ]

DURATION: Quickie ⊏——△——⊐ Super Session  (40 minutes)
WORKOUT TYPE: Endurance ⊏—△——⊐ Intervals  (Endurance)
INTESITY: Low ⊏———△—⊐ High  (55%)

1110

Song 1, Song 2, Song 3, Song 4, Song 5, Song 6, Song 7, Song 8, Song 9, Song 10, Song 11 ⟵ 1105

SPEED

0:00 —————————————— 0:40
DURATION

ESTIMATED CALORIES BURNED

[ 425 ]   DURATION: 40 minutes
         WORKOUT TYPE: Endurance Run

Pull from my music library [X]
Music streaming program [ ]   ⟵ 1120
Choose a Coach [ Coach 1 ▽ ]

[ Name Your Playlist ]  [ CREATE MY WORKOUT ]
[ Confirm and Save ]

*FIG. 11*

MUSIC STREAMING FOR ATHLETIC ACTIVITIES

FIELD OF THE INVENTION

Aspects of this invention relate generally to systems and methods for generating a training schedule and the selection of music in association therewith. In particular, aspects of this invention relate to selection of music from a music streaming program corresponding to an athletic activity.

BACKGROUND

While most people appreciate the importance of physical fitness, many have difficulty determining an appropriate exercise program for reaching their desired goal. Further, some people find it difficult to maintain an exercise regimen without some entertainment such as music to keep them motivated through the exercise program.

Athletes have found that listening to music while running may improve endurance and enjoyment of the physical activity. In particular, some types of music may be more beneficial to increasing the athletic activity of an individual than others. For example, music with fast tempos may encourage an athlete to run faster and/or farther. The use of music may help distract athletes from what might otherwise be viewed as tedious and repetitive physical activity.

Therefore, improved systems and methods to address these and other shortcomings in the art are desired.

SUMMARY

The following presents a simplified summary in order to provide a basic understanding of some aspects of the disclosure. The summary is not an extensive overview of the disclosure. It is neither intended to identify key or critical elements of the disclosure nor to delineate the scope of the disclosure. The following summary merely presents some concepts of the disclosure in a simplified form as a prelude to the description below.

One or more aspects describe systems, apparatuses, computer readable media, and methods for selecting and playing streamed audio tracks during an athletic activity. A computing device may initiate transmission of a stream of audio data comprising a plurality of audio tracks from a music streaming service, receive athletic activity data relating to a performance of an athletic activity by a user during an activity time period that includes a plurality of time intervals, determine an athletic activity level from the athletic activity data for each of the plurality of time intervals, determine a target audio track intensity corresponding to the athletic activity level, and initiate playback of a streamed audio track corresponding to the target audio track intensity.

Under certain implementations, a user input selection identifying one or more parameters corresponding to an athletic activity program is received and the target audio track intensity is determined based on the athletic activity program. Determining a target audio track intensity may include determining a target tempo corresponding to a pace of the athletic activity level. One or more sensors may be configured to detect movements of the user and provide athletic activity data relating to a performance of an athletic activity by a user. Under certain implementations, the athletic activity data of the user may include pace, distance, cadence, stride, acceleration, geolocation, heartrate, or combinations thereof. The athletic activity data may be received from a wearable device associated with the user. In some aspects, a user input selection identifying a desired athletic activity level may be received and a subsequent audio track may be selected based on the desired athletic activity level.

According to another aspect of the present disclosure, a user input selection identifying a desired athletic activity level for at least one athletic activity to be performed by a user is received and playback of a first streamed audio track from a music streaming service is initiated based on the desired athletic activity level. Athletic activity data relating to a performance of an athletic activity by the user during a first time period is received. An athletic activity level is determined from the athletic activity data and a target audio track intensity corresponding to the athletic activity level is determined. A second streamed audio track corresponding to the target audio track intensity is selected from the music streaming service regardless of the identified desired athletic activity level of the user input selection. The first time period may correspond to a duration of the first streamed audio track. A target audio track intensity may be determined based on one of tempo, melody, tone and combinations thereof.

According to other aspects of the present disclosure, a user input selection identifying one or more parameters corresponding to an athletic activity program is received, an athletic workout is generated for a user based on the user input selection, and a plurality of streamed audio tracks is selected from a music streaming service to be played during the athletic workout corresponding to the athletic workout. The athletic workout may include a plurality of athletic activity levels, and each of the plurality of streamed audio tracks is selected based on a corresponding athletic activity level. The plurality of streamed audio tracks may be selected based on user account settings associated with the music streaming service. Additionally or alternatively, the plurality of streamed audio tracks may be selected based on a target audio track intensity associated with an athletic activity level during the athletic workout.

In some embodiments of the present disclosure, an advertisement audio may be selected and played at a selected time interval, with the selected time interval based, at least in part, on an amount of completed time of the athletic workout. The selected time interval may also be selected based on sensing a pause or a slowdown of the user during the athletic workout. The advertisement audio track may be selected from a plurality of advertisement audio tracks based on a target audio track intensity corresponding to the selected time interval in the athletic workout. Additionally or alternatively, the advertisement audio track may be selected based on at least one of a geolocation of the user and one or more user information components.

In some embodiments, the present invention can be partially or wholly implemented on a computer-readable medium, for example, by storing computer-readable instructions or modules, or by utilizing computer-readable data structures.

Of course, the methods and systems of the above-referenced embodiments may also include other additional elements, steps, computer-executable instructions, or computer-readable data structures.

The details of these and other embodiments of the present invention are set forth in the accompanying drawings and the description below. Other features and advantages of the invention will be apparent from the description and drawings, and from the claims.

BRIEF DESCRIPTION OF THE DRAWINGS

A more complete understanding of the present invention and at least some features and advantages thereof may be acquired by referring to the following description and the accompanying drawings, in which like reference numbers indicate like features throughout, and wherein:

FIG. 11 illustrates another example training regimen and music playlist generator interface in accordance with example embodiments;

DETAILED DESCRIPTION

Aspects of this disclosure involve obtaining, storing, and/or processing athletic data relating to the physical movements of an athlete. The athletic data may be actively or passively sensed and/or stored in one or more non-transitory storage mediums. Still further aspects relate to using athletic data to generate an output, such as for example, calculated athletic attributes, feedback signals to provide guidance, and/or other information. These and other aspects will be discussed in the context of the following illustrative examples of a personal training system.

In the following description of the various embodiments, reference is made to the accompanying drawings, which form a part hereof, and in which is shown by way of illustration various embodiments in which aspects of the disclosure may be practiced. It is to be understood that other embodiments may be utilized and structural and functional modifications may be made without departing from the scope and spirit of the present disclosure. Further, headings within this disclosure should not be considered as limiting aspects of the disclosure and the example embodiments are not limited to the example headings.

Example Personal Training System

A. Illustrative Networks

Figure 1:
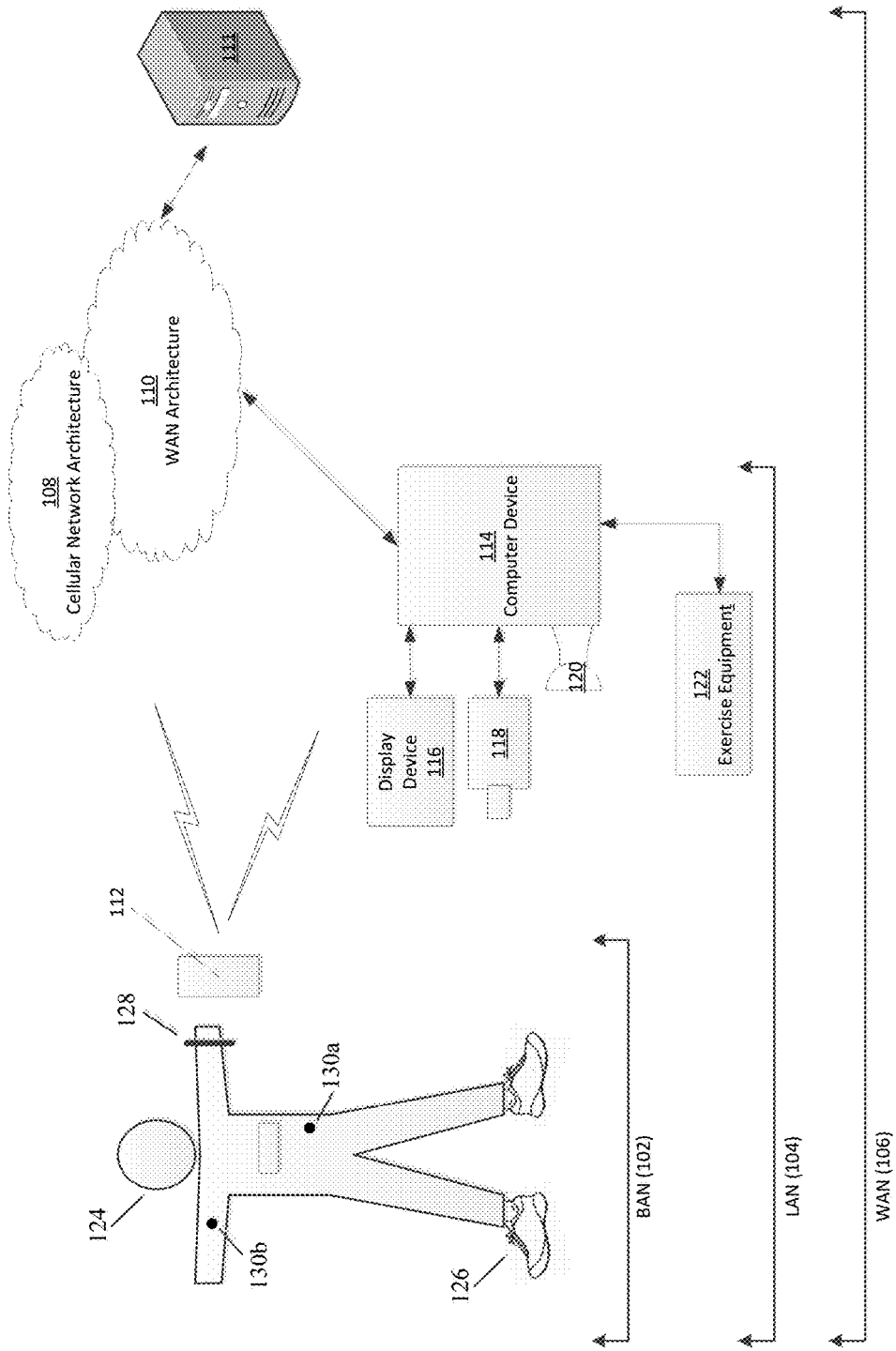
FIG. 1 illustrates an example system that may be configured to provide personal training and/or obtain data from the physical movements of a user in accordance with example embodiments.

Aspects of this disclosure relate to systems and methods that may be utilized across a plurality of networks. In this regard, certain embodiments may be configured to adapt to dynamic network environments. Further embodiments may be operable in differing discrete network environments. FIG. 1 illustrates an example of a personal training system 100 in accordance with example embodiments. Example system 100 may include one or more interconnected networks, such as the illustrative body area network (BAN) 102, local area network (LAN) 104, and wide area network (WAN) 106. As shown in FIG. 1 (and described throughout this disclosure), one or more networks (e.g., BAN 102, LAN 104, and/or WAN 106), may overlap or otherwise be inclusive of each other. Those skilled in the art will appreciate that the illustrative networks 102-106 are logical networks that may each comprise one or more different communication protocols and/or network architectures and yet may be configured to have gateways to each other or other networks. For example, each of BAN 102, LAN 104 and/or WAN 106 may be operatively connected to the same physical network architecture, such as cellular network architecture 108 and/or WAN architecture 110. For example, portable electronic device 112, which may be considered a component of both BAN 102 and LAN 104, may comprise a network adapter or network interface card (NIC) configured to translate data and control signals into and from network messages according to one or more communication protocols, such as the Transmission Control Protocol (TCP), the Internet Protocol (IP), and the User Datagram Protocol (UDP) through one or more of architectures 108 and/or 110. These protocols are well known in the art, and thus will not be discussed here in more detail.

Network architectures 108 and 110 may include one or more information distribution network(s), of any type(s) or topology(s), alone or in combination(s), such as for example, cable, fiber, satellite, telephone, cellular, wireless, etc. and as such, may be variously configured such as having one or more wired or wireless communication channels (including but not limited to: WiFi®, Bluetooth®, Near-Field Communication (NFC) and/or ANT technologies). Thus, any device within a network of FIG. 1, (such as portable electronic device 112 or any other device described herein) may be considered inclusive to one or more of the different logical networks 102-106. With the foregoing in mind, example components of an illustrative BAN and LAN (which may be coupled to WAN 106) will be described.

1. Example Local Area Network

LAN 104 may include one or more electronic devices, such as for example, computer device 114. Computer device 114, or any other component of system 100, may comprise a mobile terminal, such as a telephone, music player, tablet, netbook or any portable device. In other embodiments, computer device 114 may comprise a media player or recorder, desktop computer, server(s), a gaming console, such as for example, a Microsoft® XBOX, Sony® Playstation, and/or a Nintendo® Wii gaming consoles. Those skilled in the art will appreciate that these are merely example devices for descriptive purposes and this disclosure is not limited to any console or computing device.

Figure 2:
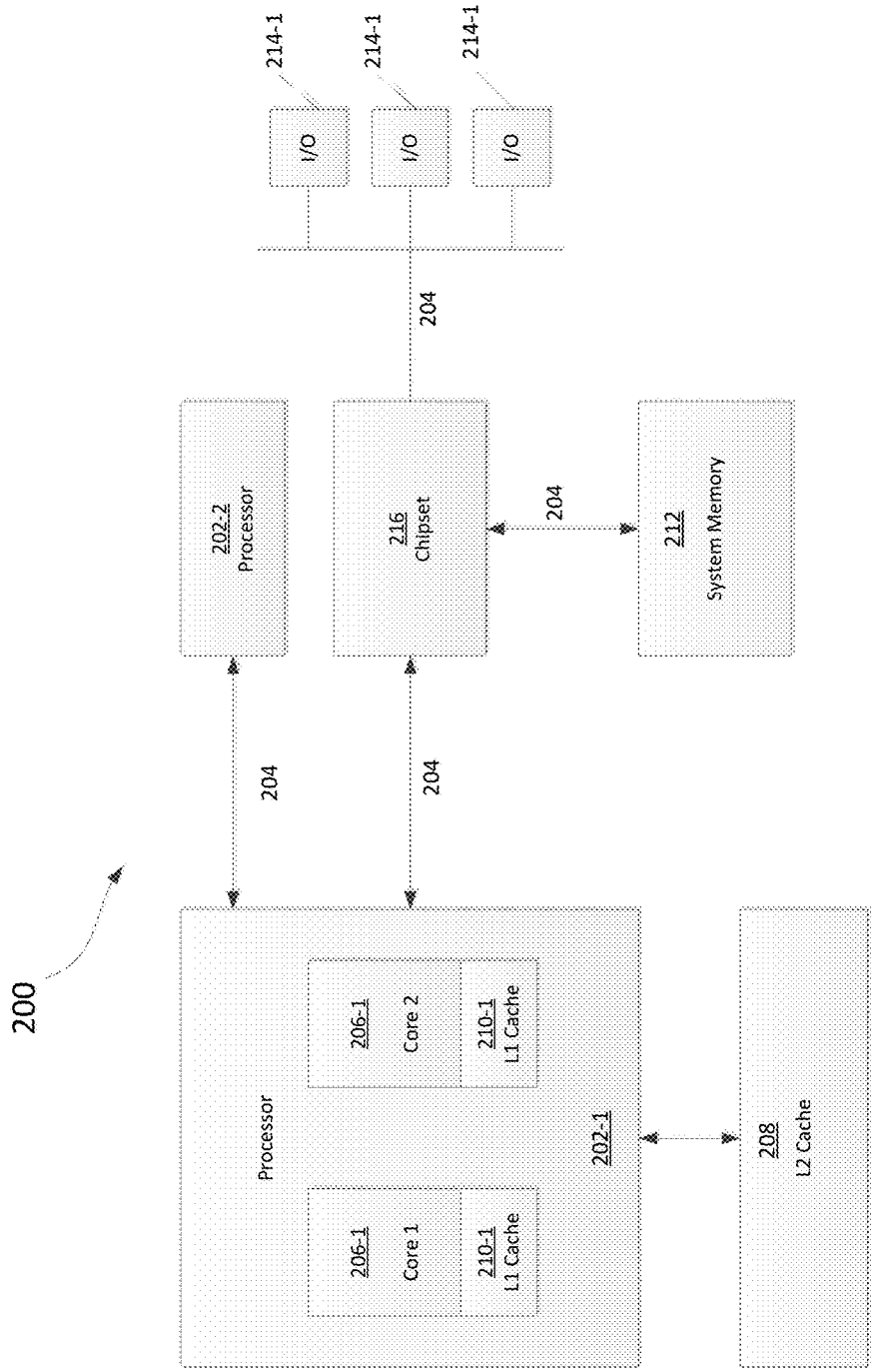
FIG. 2 illustrates an example computer device that may be part of or in communication with the system of FIG. 1.

Those skilled in the art will appreciate that the design and structure of computer device 114 may vary depending on several factors, such as its intended purpose. One example implementation of computer device 114 is provided in FIG. 2, which illustrates a block diagram of computing device 200. Those skilled in the art will appreciate that the disclosure of FIG. 2 may be applicable to any device disclosed herein. Device 200 may include one or more processors, such as processor 202-1 and 202-2 (generally referred to herein as "processors 202" or "processor 202"). Processors 202 may communicate with each other or other components via an interconnection network or bus 204. Processor 202 may include one or more processing cores, such as cores 206-1 and 206-2 (referred to herein as "cores 206" or more generally as "core 206"), which may be implemented on a single integrated circuit (IC) chip.

Cores 206 may comprise a shared cache 208 and/or a private cache (e.g., caches 210-1 and 210-2, respectively). One or more caches 208/210 may locally cache data stored in a system memory, such as memory 212, for faster access by components of the processor 202. Memory 212 may be in communication with the processors 202 via a chipset 216. Cache 208 may be part of system memory 212 in certain embodiments. Memory 212 may include, but is not limited to, random access memory (RAM), read only memory (ROM), and include one or more of solid-state memory, optical or magnetic storage, and/or any other medium that can be used to store electronic information. Yet other embodiments may omit system memory 212.

System 200 may include one or more I/O devices (e.g., I/O devices 214-1 through 214-3, each generally referred to as I/O device 214). I/O data from one or more I/O devices 214 may be stored at one or more caches 208, 210 and/or system memory 212. Each of I/O devices 214 may be permanently or temporarily configured to be in operative communication with a component of system 100 using any physical or wireless communication protocol.

Returning to FIG. 1, four example I/O devices (shown as elements 116-122) are shown as being in communication with computer device 114. Those skilled in the art will appreciate that one or more of devices 116-122 may be stand-alone devices or may be associated with another device besides computer device 114. For example, one or more I/O devices may be associated with or interact with a component of BAN 102 and/or WAN 106. I/O devices 116-122 may include, but are not limited to athletic data acquisition units, such as for example, sensors. One or more I/O devices may be configured to sense, detect, and/or measure an athletic parameter from a user, such as user 124. Examples include, but are not limited to: an accelerometer, a gyroscope, a location-determining device (e.g., GPS), light (including non-visible light) sensor, temperature sensor (including ambient temperature and/or body temperature), sleep pattern sensors, heart rate monitor, image-capturing sensor, moisture sensor, force sensor, compass, angular rate sensor, and/or combinations thereof among others.

In further embodiments, I/O devices 116-122 may be used to provide an output (e.g., audible, visual, or tactile cue) and/or receive an input, such as a user input from athlete 124. Example uses for these illustrative I/O devices are provided below, however, those skilled in the art will appreciate that such discussions are merely descriptive of some of the many options within the scope of this disclosure. Further, reference to any data acquisition unit, I/O device, or sensor is to be interpreted disclosing an embodiment that may have one or more I/O device, data acquisition unit, and/or sensor disclosed herein or known in the art (either individually or in combination).

Information from one or more devices (across one or more networks) may be used to provide (or be utilized in the formation of) a variety of different parameters, metrics or physiological characteristics including but not limited to: motion parameters, such as speed, acceleration, distance, steps taken, direction, relative movement of certain body portions or objects to others, or other motion parameters which may be expressed as angular rates, rectilinear rates or combinations thereof, physiological parameters, such as calories, heart rate, sweat detection, effort, oxygen consumed, oxygen kinetics, and other metrics which may fall within one or more categories, such as: pressure, impact forces, information regarding the athlete, such as height, weight, age, demographic information and combinations thereof.

System 100 may be configured to transmit and/or receive athletic data, including the parameters, metrics, or physiological characteristics collected within system 100 or otherwise provided to system 100. As one example, WAN 106 may comprise server 111. Server 111 may have one or more components of system 200 of FIG. 2. In one embodiment, server 111 comprises at least a processor and a memory, such as processor 206 and memory 212. Server 111 may be configured to store computer-executable instructions on a non-transitory computer-readable medium. The instructions may comprise athletic data, such as raw or processed data collected within system 100. System 100 may be configured to transmit data, such as energy expenditure points, to a social networking website or host such a site. Server 111 may be utilized to permit one or more users to access and/or compare athletic data. As such, server 111 may be configured to transmit and/or receive notifications based upon athletic data or other information.

Returning to LAN 104, computer device 114 is shown in operative communication with a display device 116, an image-capturing device 118, sensor 120 and exercise device 122, which are discussed in turn below with reference to example embodiments. In one embodiment, display device 116 may provide audio-visual cues to athlete 124 to perform a specific athletic movement. The audio-visual cues may be provided in response to computer-executable instruction executed on computer device 114 or any other device, including a device of BAN 102 and/or WAN. Display device 116 may be a touchscreen device or otherwise configured to receive a user-input.

In one embodiment, data may be obtained from image-capturing device 118 and/or other sensors, such as sensor 120, which may be used to detect (and/or measure) athletic parameters, either alone or in combination with other devices, or stored information. Image-capturing device 118 and/or sensor 120 may comprise a transceiver device. In one embodiment sensor 128 may comprise an infrared (IR), electromagnetic (EM) or acoustic transceiver. For example, image-capturing device 118, and/or sensor 120 may transmit waveforms into the environment, including towards the direction of athlete 124 and receive a "reflection" or otherwise detect alterations of those released waveforms. Those skilled in the art will readily appreciate that signals corresponding to a multitude of different data spectrums may be utilized in accordance with various embodiments. In this regard, devices 118 and/or 120 may detect waveforms emitted from external sources (e.g., not system 100). For example, devices 118 and/or 120 may detect heat being emitted from user 124 and/or the surrounding environment. Thus, image-capturing device 126 and/or sensor 128 may comprise one or more thermal imaging devices. In one embodiment, image-capturing device 126 and/or sensor 128 may comprise an IR device configured to perform range phenomenology.

In one embodiment, exercise device 122 may be any device configurable to permit or facilitate the athlete 124 performing a physical movement, such as for example a treadmill, step machine, etc. There is no requirement that the device be stationary. In this regard, wireless technologies permit portable devices to be utilized, thus a bicycle or other mobile exercising device may be utilized in accordance with certain embodiments. Those skilled in the art will appreciate that equipment 122 may be or comprise an interface for receiving an electronic device containing athletic data performed remotely from computer device 114. For example, a user may use a sporting device (described below in relation to BAN 102) and upon returning home or the location of equipment 122, download athletic data into element 122 or any other device of system 100. Any I/O device disclosed herein may be configured to receive activity data.

2. Body Area Network

BAN 102 may include two or more devices configured to receive, transmit, or otherwise facilitate the collection of athletic data (including passive devices). Exemplary devices may include one or more data acquisition units, sensors, or devices known in the art or disclosed herein, including but not limited to I/O devices 116-122. Two or more components of BAN 102 may communicate directly, yet in other embodiments, communication may be conducted via a third device, which may be part of BAN 102, LAN 104, and/or WAN 106. One or more components of LAN 104 or WAN 106 may form part of BAN 102. In certain implementations, whether a device, such as portable device 112, is part of BAN 102, LAN 104, and/or WAN 106, may depend on the athlete's proximity to an access point to permit communication with mobile cellular network architecture 108 and/or WAN architecture 110. User activity and/or preference may also influence whether one or more components are utilized as part of BAN 102. Example embodiments are provided below.

User 124 may be associated with (e.g., possess, carry, wear, and/or interact with) any number of devices, such as portable device 112, shoe-mounted device 126, wrist-worn device 128 and/or a sensing location, such as sensing location 130, which may comprise a physical device or a location that is used to collect information. One or more devices 112, 126, 128, and/or 130 may not be specially designed for fitness or athletic purposes. Indeed, aspects of this disclosure relate to utilizing data from a plurality of devices, some of which are not fitness devices, to collect, detect, and/or measure athletic data. In certain embodiments, one or more devices of BAN 102 (or any other network) may comprise a fitness or sporting device that is specifically designed for a particular sporting use. As used herein, the term "sporting device" includes any physical object that may be used or implicated during a specific sport or fitness activity. Exemplary sporting devices may include, but are not limited to: golf balls, basketballs, baseballs, soccer balls, footballs, powerballs, hockey pucks, weights, bats, clubs, sticks, paddles, mats, and combinations thereof. In further embodiments, exemplary fitness devices may include objects within a sporting environment where a specific sport occurs, including the environment itself, such as a goal net, hoop, backboard, portions of a field, such as a midline, outer boundary marker, base, and combinations thereof.

In this regard, those skilled in the art will appreciate that one or more sporting devices may also be part of (or form) a structure and vice-versa, a structure may comprise one or more sporting devices or be configured to interact with a sporting device. For example, a first structure may comprise a basketball hoop and a backboard, which may be removable and replaced with a goal post. In this regard, one or more sporting devices may comprise one or more sensors, such as one or more of the sensors discussed above in relation to FIGS. 1-3, that may provide information utilized, either independently or in conjunction with other sensors, such as one or more sensors associated with one or more structures. For example, a backboard may comprise a first sensor configured to measure a force and a direction of the force by a basketball upon the backboard and the hoop may comprise a second sensor to detect a force. Similarly, a golf club may comprise a first sensor configured to detect grip attributes on the shaft and a second sensor configured to measure impact with a golf ball.

Looking to the illustrative portable device 112, it may be a multi-purpose electronic device, that for example, includes a telephone or digital music player, including an IPOD®, IPAD®, or iPhone®, brand devices available from Apple, Inc. of Cupertino, Calif. or Zune® or Microsoft® Windows devices available from Microsoft of Redmond, Wash. As known in the art, digital media players can serve as an output device, input device, and/or storage device for a computer. Device 112 may be configured as an input device for receiving raw or processed data collected from one or more devices in BAN 102, LAN 104, or WAN 106. In one or more embodiments, portable device 112 may comprise one or more components of computer device 114. For example, portable device 112 may be include a display 116, image-capturing device 118, and/or one or more data acquisition devices, such as any of the I/O devices 116-122 discussed above, with or without additional components, so as to comprise a mobile terminal.

a. Illustrative Apparel/Accessory Sensors

In certain embodiments, I/O devices may be formed within or otherwise associated with user's 124 clothing or accessories, including a watch, armband, wristband, necklace, shirt, shoe, or the like. These devices may be configured to monitor athletic movements of a user. It is to be understood that they may detect athletic movement during user's 124 interactions with computer device 114 and/or operate independently of computer device 114 (or any other device disclosed herein). For example, one or more devices in BAN 102 may be configured to function as an all-day activity monitor that measures activity regardless of the user's proximity or interactions with computer device 114. It is to be further understood that the sensory system 302 shown in FIG. 3 and the device assembly 400 shown in FIG. 4, each of which are described in the following paragraphs, are merely illustrative examples.

i. Shoe-Mounted Device

Figure 3:
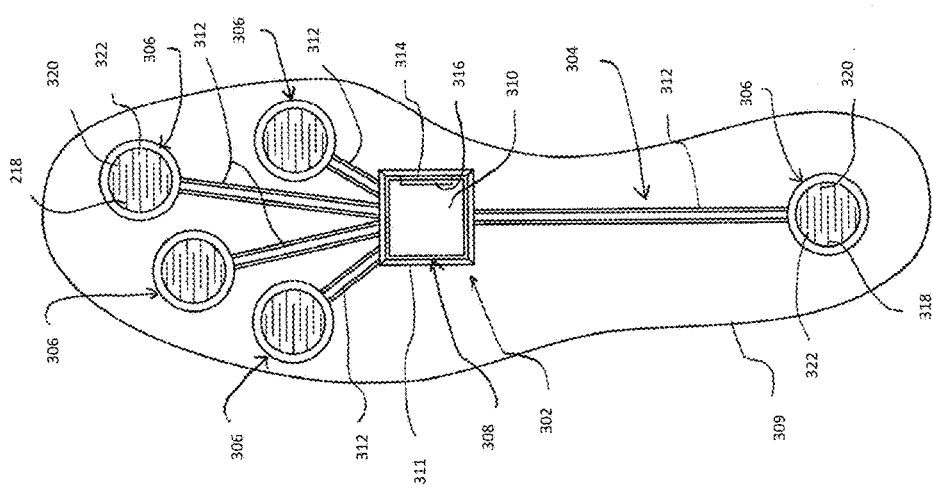
FIG. 3 shows an illustrative sensor assembly that may be worn by a user in accordance with example embodiments.

In certain embodiments, device 126 shown in FIG. 1, may comprise footwear which may include one or more sensors, including but not limited to those disclosed herein and/or known in the art. FIG. 3 illustrates one example embodiment of a sensor system 302 providing one or more sensor assemblies 304. Assembly 304 may comprise one or more sensors, such as for example, an accelerometer, gyroscope, location-determining components, force sensors and/or or any other sensor disclosed herein or known in the art. In the illustrated embodiment, assembly 304 incorporates a plurality of sensors, which may include force-sensitive resistor (FSR) sensors 306; however, other sensor(s) may be utilized. Port 308 may be positioned within a sole structure 309 of a shoe, and is generally configured for communication with one or more electronic devices. Port 308 may optionally be provided to be in communication with an electronic module 310, and the sole structure 309 may optionally include a housing 311 or other structure to receive the module 310. The sensor system 302 may also include a plurality of leads 312 connecting the FSR sensors 306 to the port 308, to enable communication with the module 310 and/or another electronic device through the port 308. Module 310 may be contained within a well or cavity in a sole structure of a shoe, and the housing 311 may be positioned within the well or cavity. In one embodiment, at least one gyroscope and at least one accelerometer are provided within a single housing, such as module 310 and/or housing 311. In at least a further embodiment, one or more sensors are provided that, when operational, are configured to provide directional information and angular rate data. The port 308 and the module 310 include complementary interfaces 314, 316 for connection and communication.

In certain embodiments, at least one force-sensitive resistor 306 shown in FIG. 3 may contain first and second electrodes or electrical contacts 318, 320 and a force-sensitive resistive material 322 disposed between the electrodes 318, 320 to electrically connect the electrodes 318, 320 together. When pressure is applied to the force-sensitive material 322, the resistivity and/or conductivity of the force-sensitive material 322 changes, which changes the electrical potential between the electrodes 318, 320. The change in resistance can be detected by the sensor system 302 to detect the force applied on the sensor 316. The force-sensitive resistive material 322 may change its resistance under pressure in a variety of ways. For example, the force-sensitive material 322 may have an internal resistance that decreases when the material is compressed. Further embodiments may utilize "volume-based resistance", which may be implemented through "smart materials." As another example, the material 322 may change the resistance by changing the degree of surface-to-surface contact, such as between two pieces of the force sensitive material 322 or between the force sensitive material 322 and one or both electrodes 318, 320. In some circumstances, this type of force-sensitive resistive behavior may be described as "contact-based resistance."

ii. Wrist-Worn Device

Figure 4:
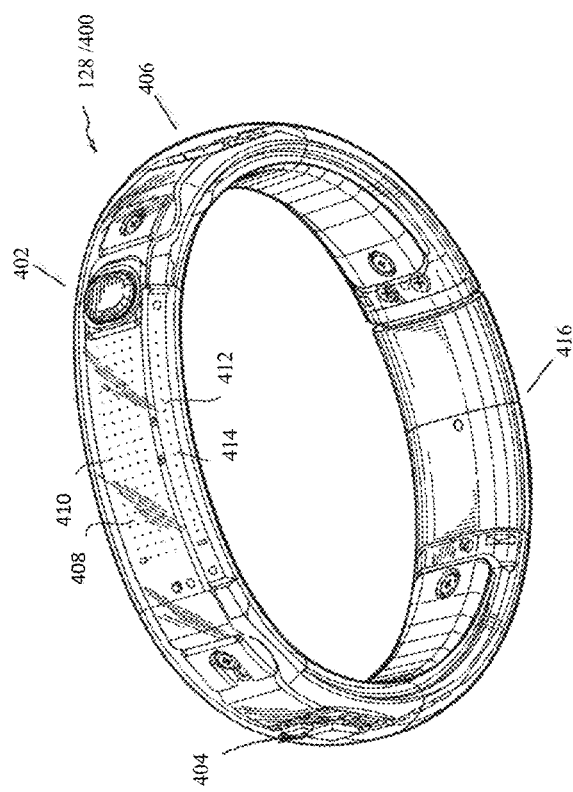
FIG. 4 shows another example sensor assembly that may be worn by a user in accordance with example embodiments.

As shown in FIG. 4, device 400 (which may resemble or comprise sensory device 128 shown in FIG. 1), may be configured to be worn by user 124, such as around a wrist, arm, ankle, neck or the like. Device 400 may include an input mechanism, such as a depressible input button 402 configured to be used during operation of the device 400. The input button 402 may be operably connected to a controller 404 and/or any other electronic components, such as one or more of the elements discussed in relation to computer device 114 shown in FIG. 1. Controller 404 may be embedded or otherwise part of housing 406. Housing 406 may be formed of one or more materials, including elastomeric components and comprise one or more displays, such as display 408. The display may be considered an illuminable portion of the device 400. The display 408 may include a series of individual lighting elements or light members such as LED lights 410. The lights may be formed in an array and operably connected to the controller 404. Device 400 may include an indicator system 412, which may also be considered a portion or component of the overall display 408. Indicator system 412 can operate and illuminate in conjunction with the display 408 (which may have pixel member 414) or completely separate from the display 408. The indicator system 412 may also include a plurality of additional lighting elements or light members, which may also take the form of LED lights in an exemplary embodiment. In certain embodiments, indicator system may provide a visual indication of goals, such as by illuminating a portion of lighting members of indicator system 412 to represent accomplishment towards one or more goals. Device 400 may be configured to display data expressed in terms of activity points or currency earned by the user based on the activity of the user, either through display 408 and/or indicator system 412.

A fastening mechanism 416 can be disengaged wherein the device 400 can be positioned around a wrist or portion of the user 124 and the fastening mechanism 416 can be subsequently placed in an engaged position. In one embodiment, fastening mechanism 416 may comprise an interface, including but not limited to a USB port, for operative interaction with computer device 114 and/or devices, such as devices 120 and/or 112. In certain embodiments, fastening member may comprise one or more magnets. In one embodiment, fastening member may be devoid of moving parts and rely entirely on magnetic forces.

In certain embodiments, device 400 may comprise a sensor assembly (not shown in FIG. 4). The sensor assembly may comprise a plurality of different sensors, including those disclosed herein and/or known in the art. In an example embodiment, the sensor assembly may comprise or permit operative connection to any sensor disclosed herein or known in the art. Device 400 and or its sensor assembly may be configured to receive data obtained from one or more external sensors.

iii. Apparel and/or Body Location Sensing

Element 130 of FIG. 1 shows an example sensory location which may be associated with a physical apparatus, such as a sensor, data acquisition unit, or other device. Yet in other embodiments, it may be a specific location of a body portion or region that is monitored, such as via an image capturing device (e.g., image capturing device 118). In certain embodiments, element 130 may comprise a sensor, such that elements 130a and 130b may be sensors integrated into apparel, such as athletic clothing. Such sensors may be placed at any desired location of the body of user 124. Sensors 130a/b may communicate (e.g., wirelessly) with one or more devices (including other sensors) of BAN 102, LAN 104, and/or WAN 106. In certain embodiments, passive sensing surfaces may reflect waveforms, such as infrared light, emitted by image-capturing device 118 and/or sensor 120. In one embodiment, passive sensors located on user's 124 apparel may comprise generally spherical structures made of glass or other transparent or translucent surfaces which may reflect waveforms. Different classes of apparel may be utilized in which a given class of apparel has specific sensors configured to be located proximate to a specific portion of the user's 124 body when properly worn. For example, golf apparel may include one or more sensors positioned on the apparel in a first configuration and yet soccer apparel may include one or more sensors positioned on apparel in a second configuration.

Figure 5:
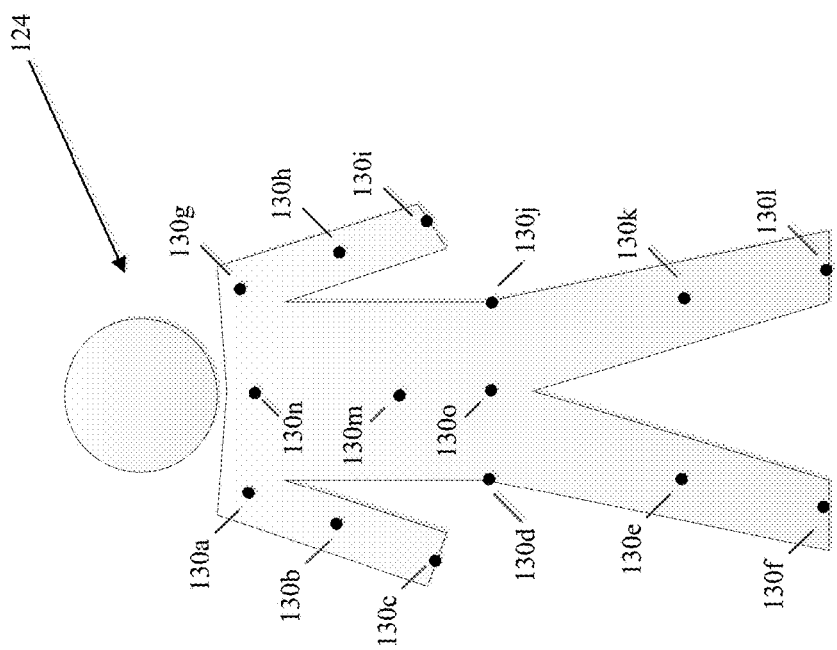
FIG. 5 shows illustrative locations for sensory input which may include physical sensors located on/in a user's clothing and/or be based upon identification of relationships between two moving body parts of the user.

FIG. 5 shows illustrative locations for sensory input (see, e.g., sensory locations 130a-130o). In this regard, sensors may be physical sensors located on/in a user's clothing, yet in other embodiments, sensor locations 130a-130o may be based upon identification of relationships between two moving body parts. For example, sensor location 130a may be determined by identifying motions of user 124 with an image-capturing device, such as image-capturing device 118. Thus, in certain embodiments, a sensor may not physically be located at a specific location (such as one or more of sensor locations 130a-130o), but is configured to sense properties of that location, such as with image-capturing device 118 or other sensor data gathered from other locations. In this regard, the overall shape or portion of a user's body may permit identification of certain body parts. Regardless of whether an image-capturing device is utilized and/or a physical sensor located on the user 124, and/or using data from other devices, (such as sensory system 302), device assembly 400 and/or any other device or sensor disclosed herein or known in the art is utilized, the sensors may sense a current location of a body part and/or track movement of the body part. In one embodiment, sensory data relating to location 130m may be utilized in a determination of the user's center of gravity (a.k.a, center of mass). For example, relationships between location 130a and location(s) 130f/130l with respect to one or more of location(s) 130m-130o may be utilized to determine if a user's center of gravity has been elevated along the vertical axis (such as during a jump) or if a user is attempting to "fake" a jump by bending and flexing their knees. In one embodiment, sensor location 130 6n may be located at about the sternum of user 124. Likewise, sensor location 130o may be located approximate to the naval of user 124. In certain embodiments, data from sensor locations 130m-130o may be utilized (alone or in combination with other data) to determine the center of gravity for user 124. In further embodiments, relationships between multiple sensor locations, such as sensors 130m-130o, may be utilized in determining orientation of the user 124 and/or rotational forces, such as twisting of user's 124 torso. Further, one or more locations, such as location(s), may be utilized as (or approximate) a center of moment location. For example, in one embodiment, one or more of location(s) 130m-130o may serve as a point for a center of moment location of user 124. In another embodiment, one or more locations may serve as a center of moment of specific body parts or regions.

Athletic Collection And Display Tools

Figure 6A:
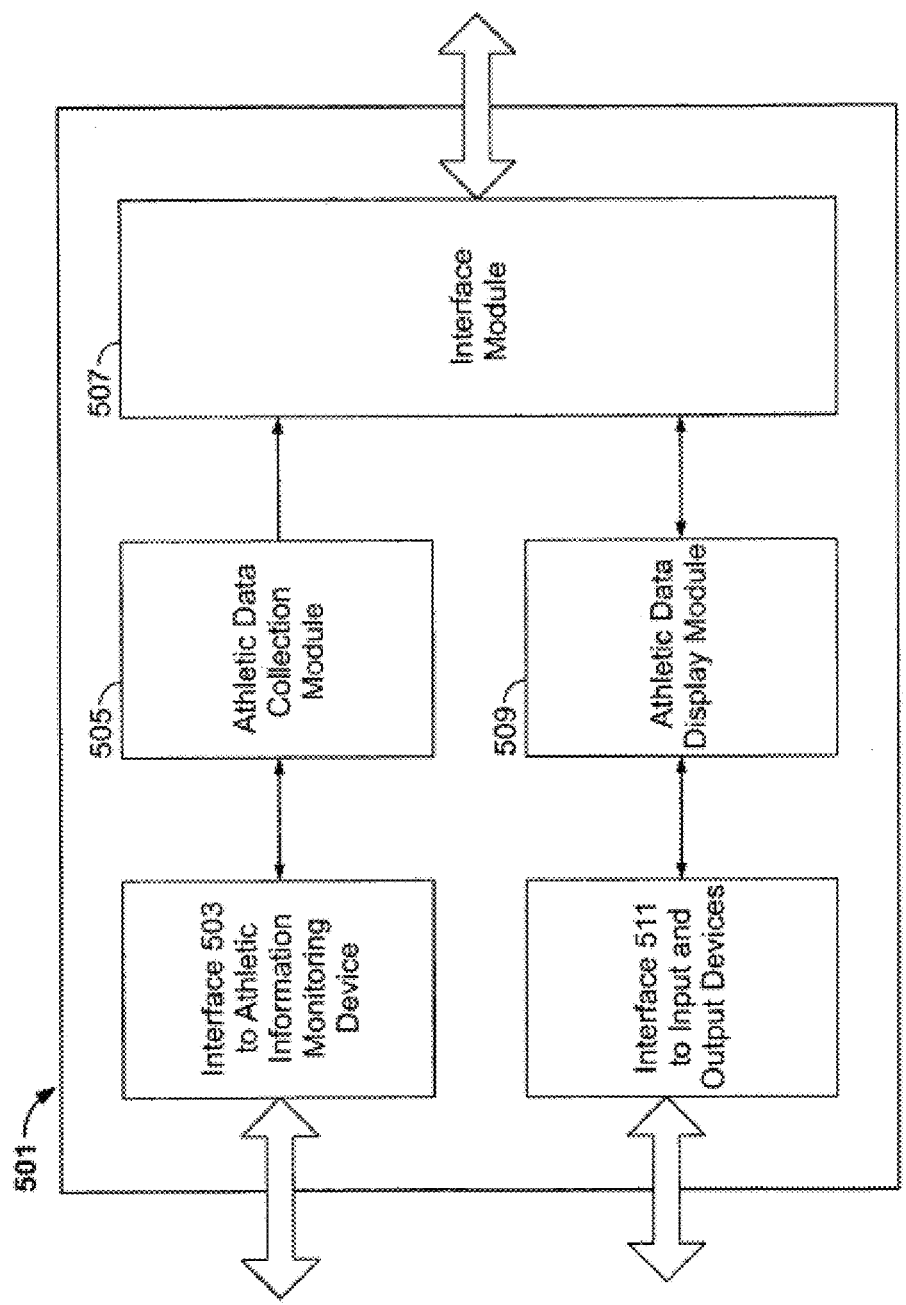
FIG. 6A illustrates an example of an athletic information collection and display device that may be employed to collect and/or display athletic data in accordance with example embodiments.

FIG. 6A illustrates an example of an athletic information collection and display device 501 that may be employed to collect and/or display athletic data according to various implementations of the invention. As will be discussed in more detail below, the athletic information collection and display device 501 may both collect and display athletic data. The athletic information collection and display device 501 may be implemented using any suitable variation of the computing device 101 previously described. In some situations, however, the information collection and display device 501 may be implemented using a desktop, laptop, personal computer, mobile computing device, and the like.

As shown FIG. 6A, the athletic information collection and display device 501 includes an interface 503 for receiving data from a portable electronic device, e.g., device 400. The interface 503 may be implemented using, e.g., electrical components, software components (such as application program interfaces (APIs)), or some combination thereof. The athletic information collection and display device 501 also has an athletic data collection module 505. With various examples of the invention, the athletic data collection module 505 may detect when device 400 or other portable electronic device storing one or more athletic data sets is connected, wirelessly or otherwise, to the athletic information collection and display device 501 through the interface 503, establish a communication session with the device 400 or other portable electronic device to retrieve the athletic data set or sets. In some implementations of the invention, the athletic data collection module 505 may delete athletic data sets from the device 400 or other portable electronic device after the athletic data sets have been retrieved.

With some examples of the invention, the athletic data collection module 505 may perform some further operations on the athletic data sets retrieved from the device 400 or other portable electronic device. For example, if the device 400 can be employed to collect athletic information from different users, then the athletic data collection module 505 may additionally prompt the user to identify himself or herself (if this information was not previously obtained by the athletic information collection and display device 501). This identification information may then be included with the retrieved athletic data sets.

As previously noted, the athletic information collection and display device 501 typically will generate sets of athletic data from information measured by one or more athletic parameter measurement devices, such as device 400. With some embodiments of the invention, however, the athletic information collection and display device 501 may instead store the raw information provided by the device 400. With these embodiments, the athletic data collection module 505 may retrieve the raw information from the device 400 or other portable electronic device, and then generate athletic data sets from the raw information itself.

The athletic data collection module 505 may be implemented by, for example, software instructions executed by a computing device, such as computer device 114. With some examples of the invention the athletic data collection module 505 may be implemented by a conventional software tool, such as a browser. Alternately, athletic data collection module 505 may be implemented by a purpose-specific software tool or by a conventional software tool enhanced to perform athletic data collection functions. For example, the athletic data collection module 505 may be implemented by a software tool that incorporates a conventional browser to perform a variety of functions.

Once the athletic data collection module 505 has collected the processed signals provided by an athletic information monitoring device, such as device 400, the athletic data collection module 505 transmits the athletic data set to an athletic data display configuration device 601 through an interface module 507. The athletic information collection and display device 501 may communicate with the athletic data display configuration device 601 through a conventional network, such as the Internet. With these configurations, the interface module 507 may be implemented using any conventional type of network interface, such as a network interface card. Of course, any type of desired hardware or software combination alternately may be used to allow the athletic data collection module 505 to send the collected athletic data to the athletic data display configuration device 601. With some implementations of the invention, the athletic data collection module 505 may automatically forward collected athletic data to the athletic data display configuration device 601. For example, the athletic data collection module 505 may attempt to forward collected athletic data to the athletic data display configuration device 601 immediately after collection, at a prescheduled interval, upon the detection of a network connection to the athletic data display configuration device 601, or some combination thereof. Alternately or additionally, the athletic data collection module 505 may prompt a user to specify when collected athletic data is sent to the athletic data display configuration device 601.

Figure 6B:
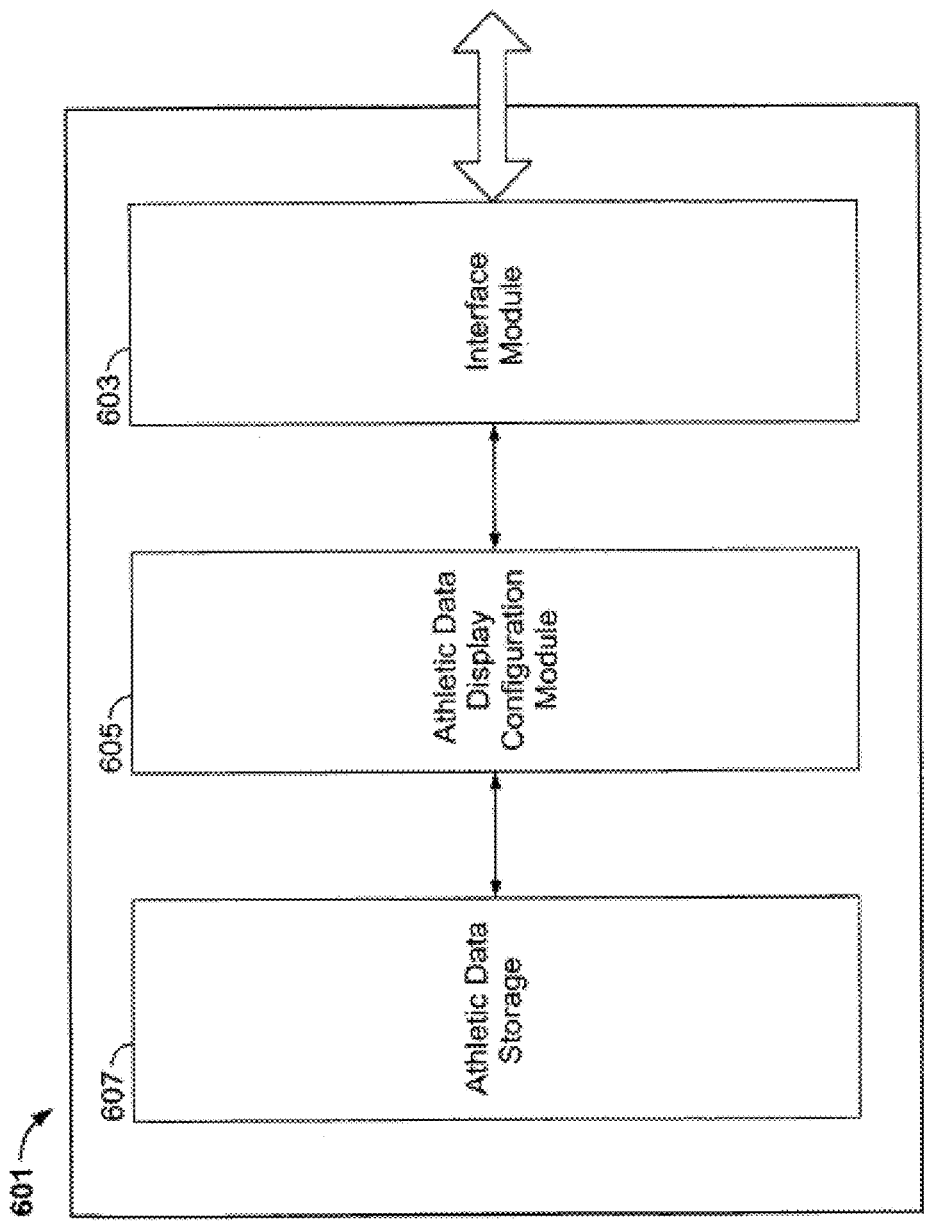
FIG. 6B illustrates an example of an athletic data display configuration device that may be employed in accordance with example embodiments.

FIG. 6B illustrates an example of an athletic data display configuration device 601 that may be employed according to various examples of the invention. As seen in this figure, the athletic data display configuration device 601 includes an interface module 603 for communicating with the athletic information collection and display device 501. As previously noted, the athletic information collection and display device 501 may communicate with the athletic data display configuration device 601 through a conventional network, such as the Internet. With these configurations, the interface module 603 may be implemented using any conventional type of network interface, such as a network interface card. Of course, any type of desired hardware or software combination alternately may be used to allow the athletic data display configuration device 601 to communicate with the athletic information collection and display device 501.

The athletic data display configuration device 601 also includes an athletic data display configuration module 605, and an athletic data storage 607. When the interface 603 of the athletic data display configuration device 601 receives athletic data from the athletic information collection and display device 501, it provides the received athletic data to the athletic data display configuration module 605. The athletic data display configuration module 603 may then store the athletic data in the athletic data storage 607 for future use. As will be discussed in more detail below, the athletic data display configuration module 605 also will retrieve athletic data from the athletic data storage 607, and configure the retrieved athletic data for display through one or more user interfaces in a manner that is meaningful to a user.

Returning now to FIG. 6A, when a user wishes to view information relating to his or her athletic activities (or the athletic activities of another, as will be discussed in more detail below), the user submits this request to the athletic information collection and display device 501. More particularly, the user can employ conventional input and output devices, such as a keyboard, mouse, display and the like. The display request is then provided to an athletic data display module 509 through a conventional interface input/output interface 511. As well known in the art, the interface input/output interface 511 may be implemented using any desired combination of hardware and software components, such as conventional application programming interfaces (APIs) used to detect and process input from input devices, and to send data to and otherwise control output devices.

With some examples of the invention, the athletic data display module 509 may be implemented using any conventional tool for receiving input to request and control the display of data, and then subsequently displaying the data in the manner requested. For example, the athletic data display module 509 may be implemented using a conventional browser program, executing on a computing device, such as device 114. In still other embodiments of the present disclosure, the athletic data display module 509 may be implemented by, for example, a purpose-specific software tool for displaying athletic data. In yet still other embodiments of the present disclosure, the athletic data display module 509 may generate an interface that is provided to the user via one or more series of webpages (e.g., a website).

As will be discussed in more detail below, when a user activates the athletic data display module 509, he or she is provided with a user interface prompting the use to select what collected athletic data he or she wishes to view, the format in which the user wishes to view the collected athletic data, etc. This user interface may be generated by the athletic data display module 509, the athletic data display configuration module 605, or some combination thereof. When a user employs the provided user interface to submit a request to view athletic data, the athletic data display module 509 relays the request to the athletic data display configuration module 605. In response, the athletic data display configuration module 605 configures the requested athletic data for display by the athletic data display module 509. For example, as will be discussed in more detail below, a user may request to view a total amount of athletic activity performed by a user over a period of time, such as the athletic activity performed each day in a one week period. In response, the athletic data display configuration module 605 will retrieve the relevant athletic activity data from the athletic data storage 607. It will then configure the retrieved athletic activity data to be displayed through a desired image (e.g., a graph), and provide the configured athletic data to the athletic data display module 509 for display to the user.

It should be noted that, with some embodiments of the invention, the data display configuration functions may be divided between the athletic data display module 509 and the athletic data display configuration module 605. For example, if the athletic data display module 509 is implemented by a simple browser, then the athletic data display module 509 may serve as a "thin client" for the athletic data display configuration module 605. That is, all of the data display configuration functions may be performed by the athletic data display configuration module 605. The athletic data display module 509 will then only display the information provided to it. Alternately, if the athletic data display module 509 is implemented by a purpose-specific software tool, then most or all of the data display configuration functions may be performed by the athletic data display module 509. With these examples, the athletic data display configuration module 605 may be used only to store and retrieve athletic data from the athletic data storage 607.

Figure 7:
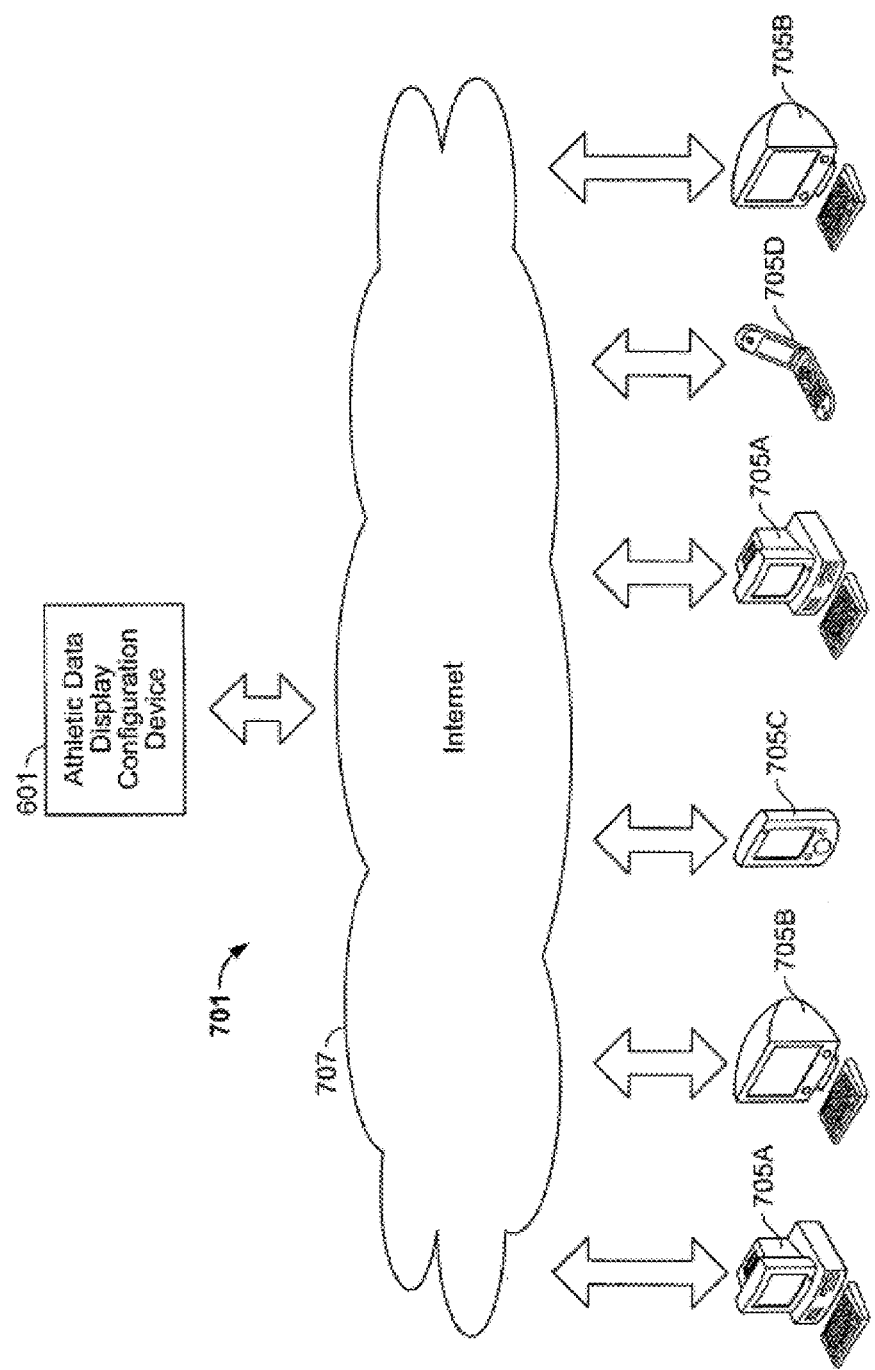
FIG. 7 illustrates a network including an athletic data display configuration device and a plurality of client devices of the type that may be employed in accordance with example embodiments.

Typically, the athletic data display configuration device 601 will be implemented at a remote location from the athletic information collection and display device 501. The athletic information collection and display device 501 then may be connected to the athletic data display configuration device 601 through an electronic communication network, as previously noted. The electronic communication network may be a public network, such as the Internet, a private network, or include some combination of both. For example, FIG. 7 illustrates a network 701 including an athletic data display configuration device 601 and a plurality of client devices 705 for collecting and/or displaying athletic data. These client devices 705 may include various types of computing devices (e.g., devices 705A-D), such as laptops, personal computers, tablets, mobile computing devices, etc. Of course, various examples of the invention may alternately or additionally include any other desired electronic device that can be configured to collect and/or display athletic data as discussed above.

It should be appreciated that a client device 705 may perform an athletic data collection function, an athletic data display function, or both. That is, while the example of the athletic information collection and display device 501 described above is capable of both collecting and displaying athletic data, some client devices 705 may only collect athletic data. Further, some client devices may only display athletic data. For example, a user may employ a GPS-equipped smart telephone to collect athletic data and transmit the collected athletic data to the athletic data display configuration device 601. The user may then employ a personal computer equipped with only a conventional browser to subsequently download and display the collected athletic data.

Visualization of Athletic Activity

Figure 8:
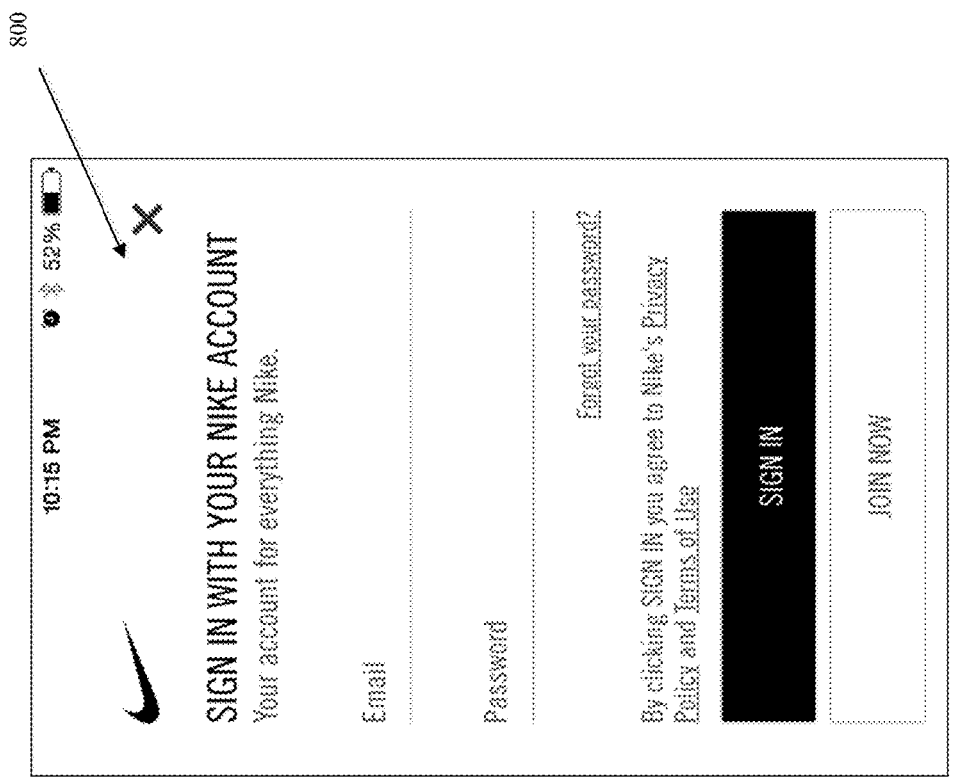
FIG. 8 shows an example display of a login interface presented by a display screen of a computer device in accordance with example embodiments.

In response to receiving a request to review athletic information from a user via the athletic data display module 509, the athletic data display configuration module 605 may determine or confirm the user's identity. FIG. 8 illustrates an example of a user interface response that might take place as a result of a user requesting to review athletic information. In this illustrated example, a login interface may be presented to the user. Login interface 800 may include an overlay screen portion or text box(es) that request information from the user in order to view their athletic information. For example, as illustrated in FIG. 8, text boxes may be displayed in a portion of login interface 800 that request entry of the user's account login and password. The request(s) for information may be provided to the user in any desired manner or format without departing from the present disclosure, such as via text input boxes, drop down listings, etc.

In some embodiments, one or more text boxes displayed in login interface 800 may be pre-populated with the requested user information. For example, if a user has previously created a user account with the entity offering maintaining (or storing) the users athletic information (e.g., a Nike+ account), the athletic data display configuration device 601 may retrieve the requested user information from a cookie (or other data storage), and display the user information in the one or more text boxes when the login interface is initially displayed to the user. Once all necessary or desired information is input by the user, the user may select the "Sign In" icon (or in any other desired manner) to access their collected athletic information. Optionally, if desired, the user may access their collected athletic information without the need for input of this type of additional registration information, without departing from the present disclosure. This may be done, for example, if account information for the user (e.g., username, email, password, etc.) and/or other user ID information has already been stored (e.g., in a cookie).

If a user does not have a user account, the user may register for a new user account. The user may be provided with a registration interface that requests information from the user in order to generate a user account. For example, the registration interface may include text boxes that request entry of the user's name, email, a user ID, password, gender, zip code, mobile phone number, and other desired information. In this example, the system may store this information for subsequent use.

After the athletic data display configuration module 605 has confirmed the user's identity, the athletic data display configuration module 605 may then retrieve the athletic data associated with the user from the athletic data storage 607. Next, the athletic data display configuration module 605 may prepare a user interface for displaying the requested athletic data, and transmit the user interface with the athletic data to the athletic data display module 509 for display to the user.

Example Initial User Interface

Figure 9:
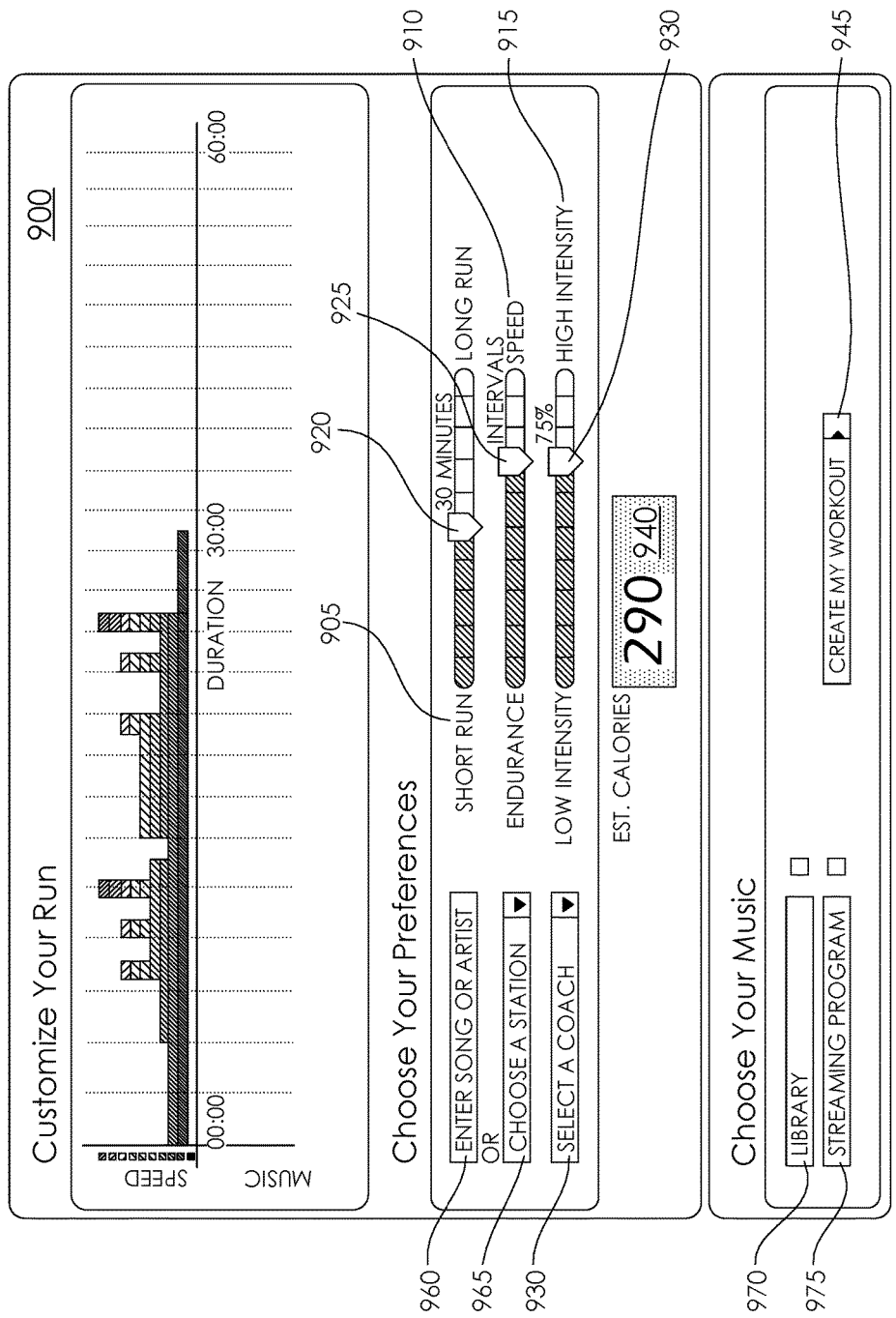
FIG. 9 illustrates an example training regimen and music playlist generator interface in accordance with example embodiments.

FIG. 9 illustrates an example of an initial user interface 900 that may be provided to a user according to various implementations of the invention and through which an athlete may specify athletic activity, e.g., athletic training, parameters and request an automatically generated schedule in accordance with those parameters. For example, interface 900 provides an athlete with the ability to define factors such as distance 905, attribute to be developed 910 and intensity level 915. Each of factors 905, 910 and 915 may be adjusted or defined using a slider bar, for example. Other control elements that may be used to define these parameters 905, 910 and 915 include drop down menus, radio buttons and/or combinations thereof. The current setting of each of parameters 905, 910 and 915 may be displayed next to position indicators 920, 925 and 930. For example, distance parameters 905 may indicate that the athlete has selected a 30-minute run while skill parameter 910 indicates the workout focus near indicator 925. The workout focus may specify endurance, interval (i.e., a mix of endurance and speed) and speed. Further, a 75% intensity level is indicated near position indicator 930. Other parameters may also be used for automatic creation and customization of a workout including age, weight, types of athletic activity (to create combination workouts involving multiple types of athletic activity), resting heart rate, time of day and intended workout goal (e.g., fat burn vs. cardio). Aspects of the initial user interface 900 may similarly be used to generate other types of athletic activity training programs and schedules.

In addition to the parameters 905, 910 and 915 described above, a user may further select a particular coach or athlete with which to train using drop-down menu 930. For example, if a user selects a well-known athlete (e.g., a celebrity) as the coach or training athlete, the training generator module may create a training regimen that simulates one which the well-known athlete would perform or has performed. Training information for the selected athlete and other celebrities or athletes may be accessed from a remote database, for example. The selected athlete's training program may be modified based on parameters 905, 910 and 915 specified by the user. If a user has selected 50% intensity, for instance, a selected athlete's training program may be decreased by 50% run speed or other corresponding intensity activity attribute (e.g., weight if the training includes weightlifting or steps per minute if the training includes an elliptical machine). Additionally, if the athlete has indicated he or she would like to concentrate on endurance, the selected athlete's training program may be lowered in intensity while increased in duration. Once the one or more of parameters 905, 910, 915 and 930 have been defined, the user may select the create workout option 945 to have the training generator module automatically create a customized workout in accordance with the defined parameters.

Interface 900 may include a training schedule graph 935 to illustrate the user's customized workout in addition to an estimate of a number of calories that will be burned through the customized workout in display area 940. In one or more arrangements the estimated number of calories burned provided in display area 940 may be determined or generated based on the training parameters 905, 910, 915 and 930 defined. For example, the system may calculate an estimated number of calories that will be burned for a 30 minute interval run at 75% intensity. In another example, the system may calculate the estimated calorie burn based on a music parameter, song or music playlist selection. For example, the system may determine, based on previous workouts, that the user typically exceeds a specific goal or target number of calories (e.g., an expected number of calories burned determined based on only the non-music training parameters specified) whenever a particular song, type of song, artist, genre, etc. is played. Accordingly, the system may increase the estimated number of calories burned for that segment of the workout based on an average number of calories burned during the song (e.g., based on a workout history), an average percentage by which a target number of calories is exceeded and the like and the like.

Additionally or alternatively, training schedule graph 935 is presented as a chart of time vs. speed and thus provides a visual representation of the athletes created workout. If the user wishes to change the workout, the user may do so by modifying parameters 905, 910 and 915. Alternatively or additionally, a user may manually adjust specific portions of the workout by adjusting the speed levels, for example, for a specific interval of time. Graph 935 may be illustrated in terms of other or additional parameters. For example, a chart of speed vs. time vs. calories may be displayed in a three dimensional graph. Colors of the graph may be indicative of intensity. Accordingly, higher speeds may be indicated by red or bright colors while lower speeds may be represented by black or darker colors. In one or more arrangements, hovering or otherwise interacting with one of the bars in graph 935 may result in the generation of a pop-up window displaying details about that segment of the workout.

Allowing an athlete to customize their workout may increase the investment and dedication the athlete feels towards exercising. Additionally, giving the athlete such control over their workout allows the athlete to generate a workout that is commensurate with his/her own estimation of the athlete's athletic ability. Oftentimes, an athlete may be overwhelmed by generic workouts that are directed to moderately fit or athletic individuals. In one or more configurations, a user may be able to specify an amount of calories that he or she wishes to burn by entering the value in calories burned display area 940. Other parameters 905, 910 and 915 may be automatically adjusted to reach the burned calories goal. For example, the duration of the workout may be increased or decreased.

Figure 10:
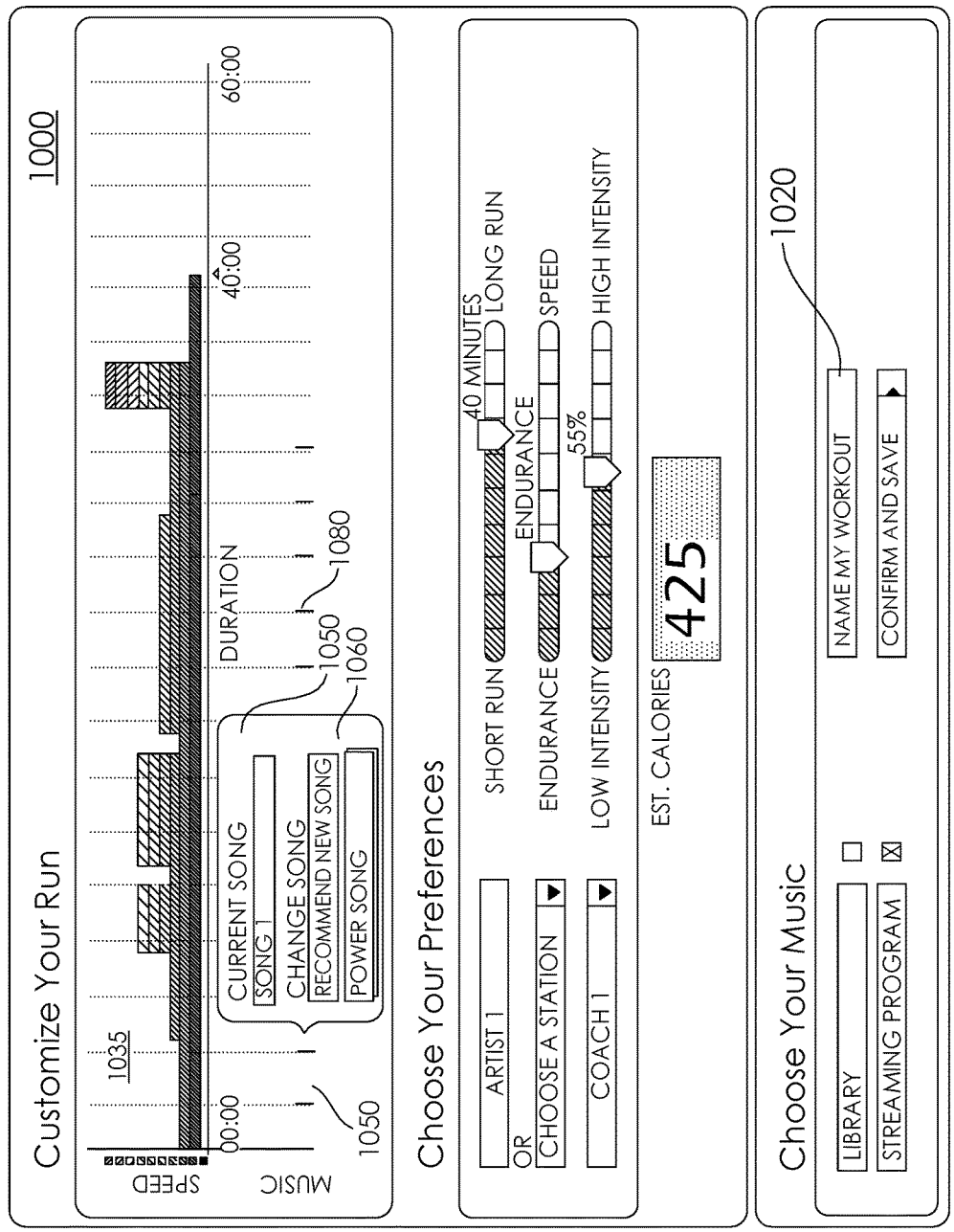
FIG. 10 illustrates another example training regimen and music playlist generator interface in accordance with example embodiments.

FIG. 10 illustrates a workout interface 1000 displaying a generated workout created based on user specified parameters such as those displayed in interface 900 (FIG. 9). For example, interface 1000 may display a 40 minute workout of moderate intensity (55%) that is focused on endurance rather than speed. Interface 1000 further indicates that the workout is based on a selection of a particular athlete such as a famous or well-known athlete or coach with which the user would like to train. A pop-up window 1050 may be included displaying details of a song that will be played during a particular segment of the workout. Music incorporation via a music selection module will be described in greater detail below.

FIG. 11 illustrates a workout interface 1100 according to another embodiment. Workout interface 1100 shows workout regimen 1105 along with selected songs 1110 to be played during the workout. Different options may be provided in interface 1100 (in contrast to interface 900 of FIG. 9 and interface 1000 of FIG. 10). For example, interface 1100 might not include a parameter for selecting speed vs. endurance, but may include an option 1120 to add coaching.

In one example of coaching, several voice recordings may be downloaded to a workout device (e.g., a music player, workout machine) and played during the user's workout to provide additional motivation. If the athlete is slowing down, the device may play a voice recording that says "Don't slow down now! You are almost there!" or similar encouraging/motivational remarks. Alternatively, the voice recordings may provide remarks of congratulations or positive reinforcement such as "Great job!" or "You are really moving!" In addition or as an alternative to voice recordings, the device may have speech generation hardware, software and/or firmware to produce speech based on text. Coaching may also be used to modify or recommend a training regimen based on a user's current or past performance.

Figure 12:
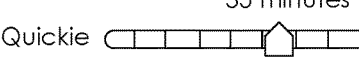
FIG. 12 illustrates another example training regimen and music playlist generator interface having mood and music type parameter selection options in accordance with example embodiments.

FIG. 12 illustrates another embodiment of a workout regimen generation interface 1200 that may be used to specify workout preferences. Interface 1200 may include parameters for specifying a desired workout length 1205, number of calories burned 1210, pace 1215, pace fluctuations 1220, mood/level of energy 1225 and type of music 1230. Specifically, pace 1215 may define the speed of the workout while pace fluctuations 1220 may be used to define whether the pace will fluctuate (e.g., intervals) over the workout. Fluctuations may require further endurance or strength and thus may help burn more calories. Mood/level of energy 1225 may be used to help the regimen generation system determine a difficulty of the workout to create. For example, if an athlete is not feeling as motivated, the workout may be less strenuous. If, on the other hand, the athlete is upbeat and has a lot of energy, the workout regimen generation system may take advantage of the energy by creating a more difficult workout for the user. Additionally or alternatively, the mood/level of energy 1225 may be used to determine the type of music to be associated with the workout, as described in further detail herein.

Figure 13:
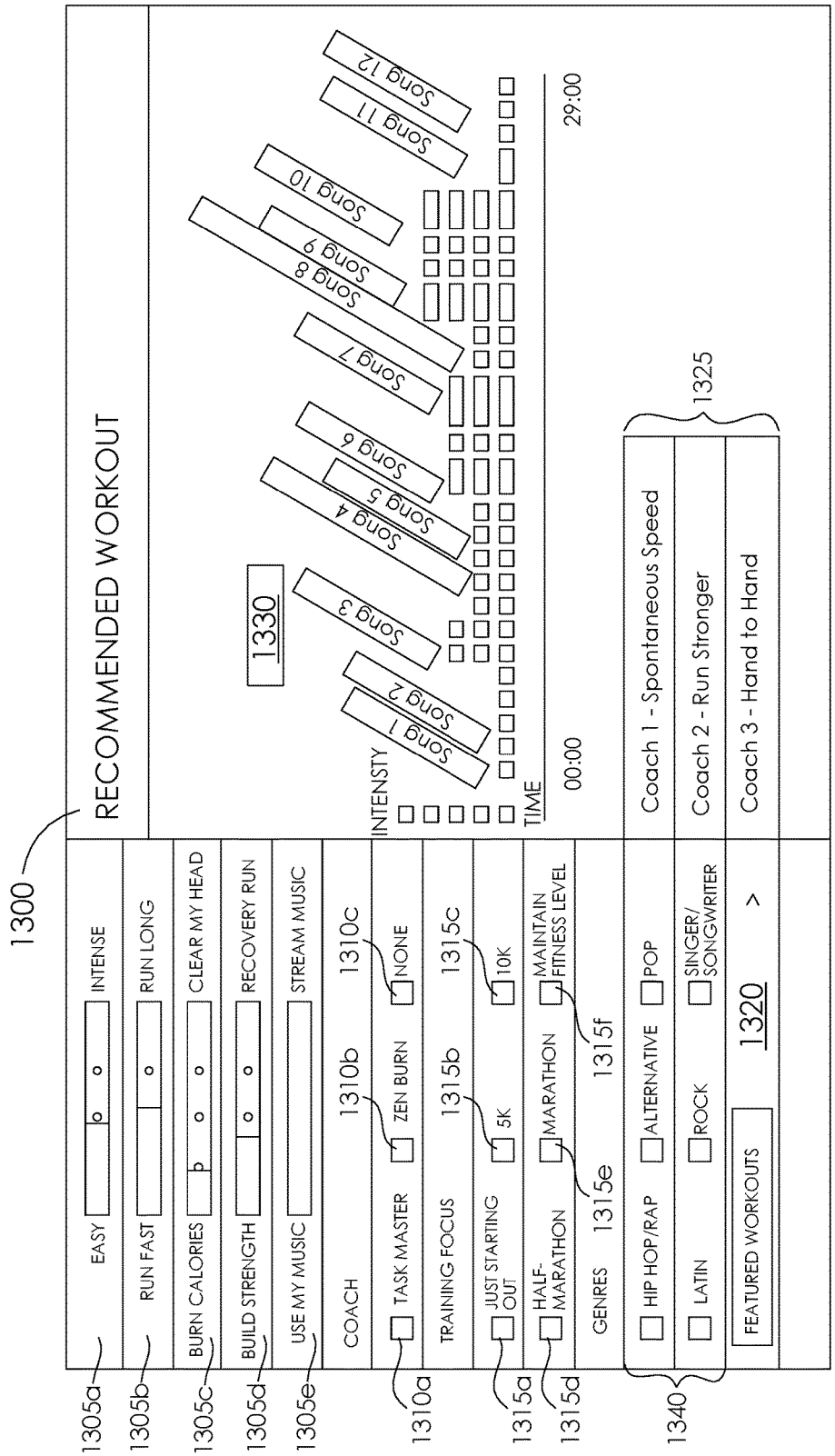
FIG. 13 illustrates another example training regimen and music playlist generator interface having coaching, training focus and music genre selection options in accordance with example embodiments.

FIG. 13 illustrates yet another embodiment of an interface 1300 that may be used to define workout preferences. For example, regimen creation parameters 1305 may include workout intensity 1305a, speed vs. distance option 1305b, calories vs. relaxation option 1305c, strength vs. recovery option 1305d and a music selection manner option 1305e. Each of options 1305 may be controlled via a slider bar that may be moved to various positions between each extreme. In one example, a user may specify that he or she would like a workout that focuses 50% on distance and 50% on speed. Similarly, if a user would like to focus on calorie burning, a slider may be positioned closer to the calorie burning side of option 1305c. Additionally or alternatively, a user may select a type of coach with which to generate the workout. Coaching types may include a strict coach such as a taskmaster 1310a or a coach with a more relaxed attitude such as Zen master 1310b. If a user does not wish to have coaching, the user may select option 1310c.

In interface 1300, an athlete may further select a training focus. For example, a user may focus his or her training on beginning athletic activity 1315a, running a 5K 1315b, running a 10K 1315c, running a half-marathon 1315d, running a marathon 1315e and/or maintaining a current fitness level 1315f. A current fitness level may be determined from stored workout data. Training regimens for running a specified distance may include running workout of progressively increasing distance and/or speed. If a user would like to choose a pre-made workout, he or she may select featured workout option 1320 and select one of pre-generated workouts 1325. Option 1305e for choosing a manner of selecting music to accompany the workout may be provided, as discussed in further detail with respect to music playlist generation. Once the desired options have been selected, a recommended or proposed workout 1330 may be displayed in chart form.

Additionally, in each of the interfaces illustrated in FIGS. 9-13, a user may choose to name and save their workout by entering a desired name in a text box such as text box 1020 of FIG. 10. Interfaces may further include various music selection parameters as is discussed in greater detail below.

Figure 14:
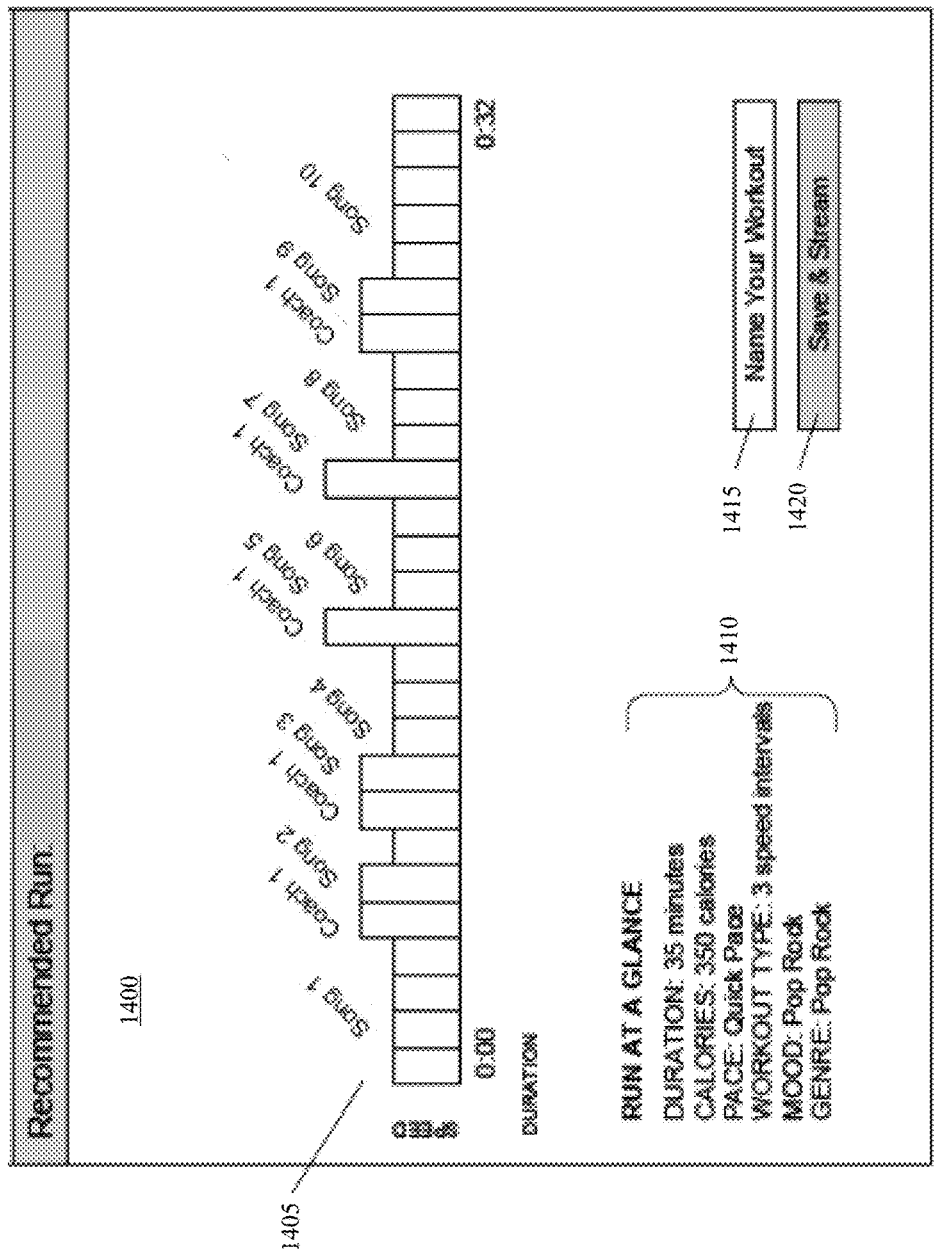
FIG. 14 illustrates a recommended run summary displaying various attributes of the recommended workout in accordance with example embodiments.

FIG. 14 illustrates a recommended workout summary 1400 displaying a planned workout graph 1405 charting time versus speed. Workout information 1410 may be displayed in textual form to provide a summary of various workout attributes such as duration, calories, pace, workout type, mood, genre of music and the like. The workout may be structured to provide coaching segments and music selections at various parts of the workout. The coaching segments and music selections may alternate, be in combined form, or be in random order or any other arrangement. The workout may be named using option 1415 and/or saved using option 1420. Once saved, the workout may further be streamed to an athletic workout device such as a music player or a performance monitoring device (e.g., a pedometer, etc.)

Figure 15:
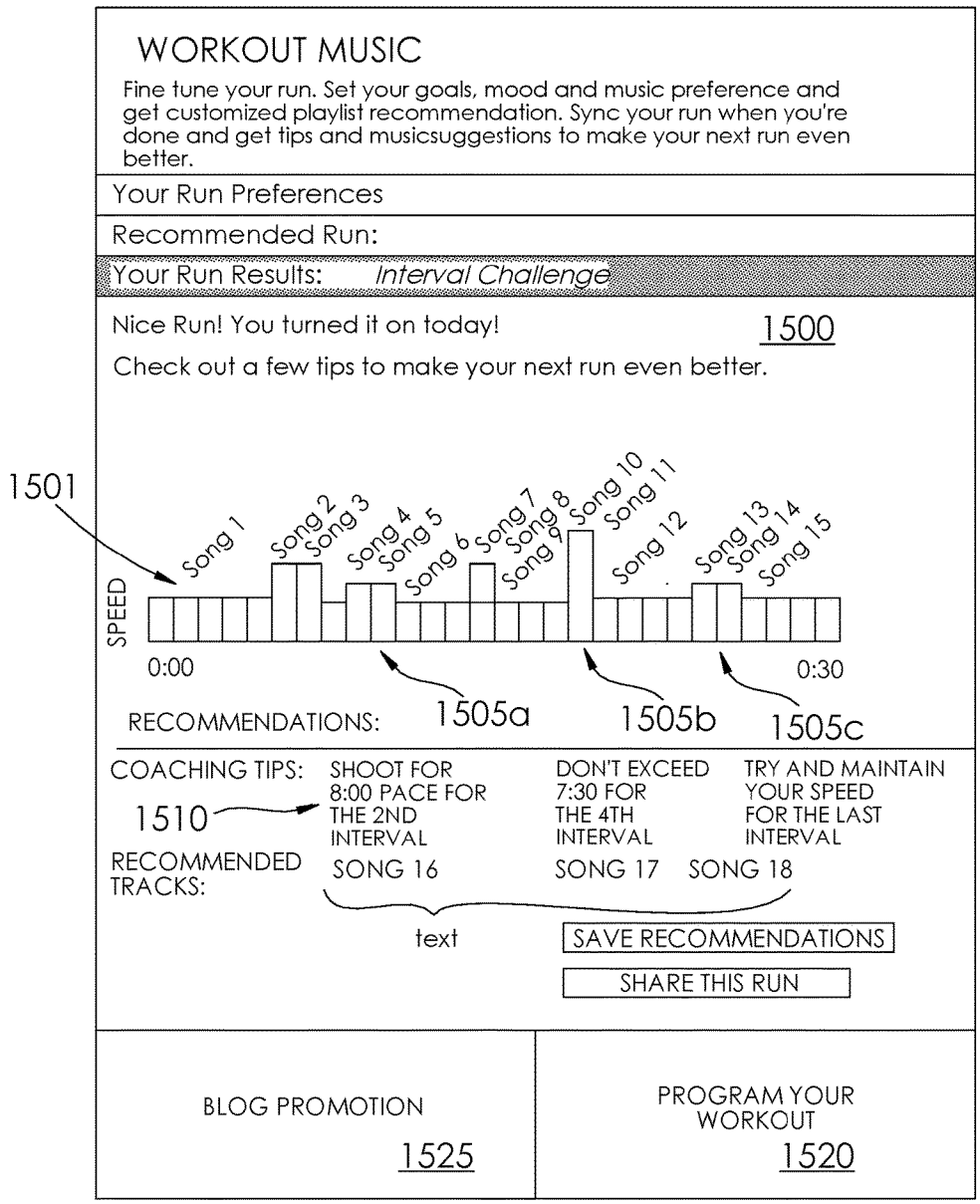
FIG. 15 illustrates a workout summary report indicating portions of the workout that may be improved and improvement in accordance with example embodiments.

FIG. 15 illustrates an interface 1500 after a user has performed a workout. Various portions 1505 of workout 1501 may be highlighted (e.g., by a different color) to indicate portions of the workout that the user may improve. Coaching or recommendation tips 1510 may be displayed to help the user achieve better results. Different recommendations or suggestions 1510 may be provided for the different highlighted portions 1505. The user may further be provided options 1520 and 1525 to program a workout (e.g., a new workout) or to post comments or a report about the completed workout, respectively.

Figure 16:
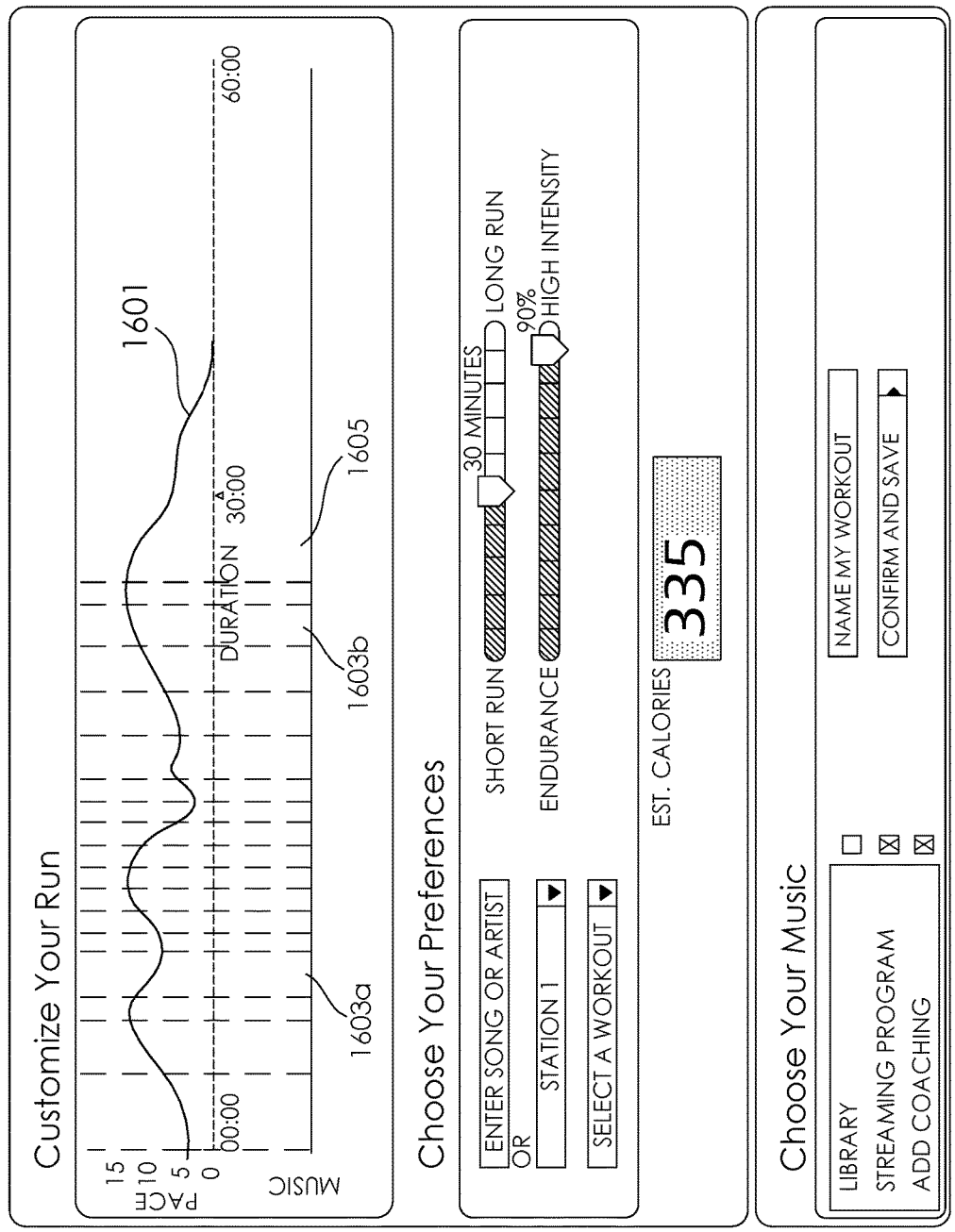
FIG. 16 illustrates a run curve with songs of a music playlist mapped thereto in accordance with example embodiments.

FIG. 16 illustrates a graph of a customized workout graph charting pace versus time. Music bar 1605 may display a plurality of demarcations indicating the beginning of songs in a music playlist generated for the customized workout. Accordingly, songs may be mapped to various portions of workout 1601. The mapping may be performed randomly or may be determined according to various rules, as described herein.

Music Playlist Selection and Generation

The training schedule produced by the training generator module described herein may be accompanied by a music selection module that generates a playlist of music to be played during the customized workout. FIG. 9 illustrates interface 900 wherein a user may select various music selection parameters including song or artist entry form 960, station selection menu 965, library music source option 970 and streaming music program option 975. The music selection parameters may be used to select a music streaming station from one or more online music streaming services and/or music from a library. Audio tracks from an online music streaming program via option 975 may be provided over a network such as the Internet (via a streaming module). Song/artist entry block 960 provides a way for an athlete to identify a particular song or artist that the athlete likes. Upon entry of a song in form 960, for example, the music generator module may add the selected song and similar songs thereto to a playlist for playing during the corresponding workout. Alternatively, if an artist is entered in form 960, the music generator may identify and select songs by that artist and/or songs by similar artists.

Similarity of songs or artists may be determined by the training module based music purchase and selection activity of other users and/or using one or more algorithms of the music streaming program. Thus, the training program may transmit the various music selection parameters inputted by the user in interface 900 to the music streaming program to initiate generation of a workout program. Additionally or alternatively, the training module may generate one or more rules or song selections for the music streaming program to create the music playlist. In some examples, if users who purchase songs by a first artist also generally purchase songs by a second artist, an athlete who specifies the first artist as a desired artist or a song by the first artist as a desired song, the second artist's songs might also be identified and selected by the music selection module due to a presumed similarity. Similarity might also be determined using other methods such as by comparing tempo (e.g., beats per minute), melody, tone and the like. Song selections may also be determined that may be motivating in nature or motivating in particular for the particular athlete. Additionally, song selection may be performed on the fly (e.g., during the workout in which the songs are to be played) or prior to a workout. For example, songs may be selected based on a sensed activity level during the workout, as described herein.

Figure 18B:
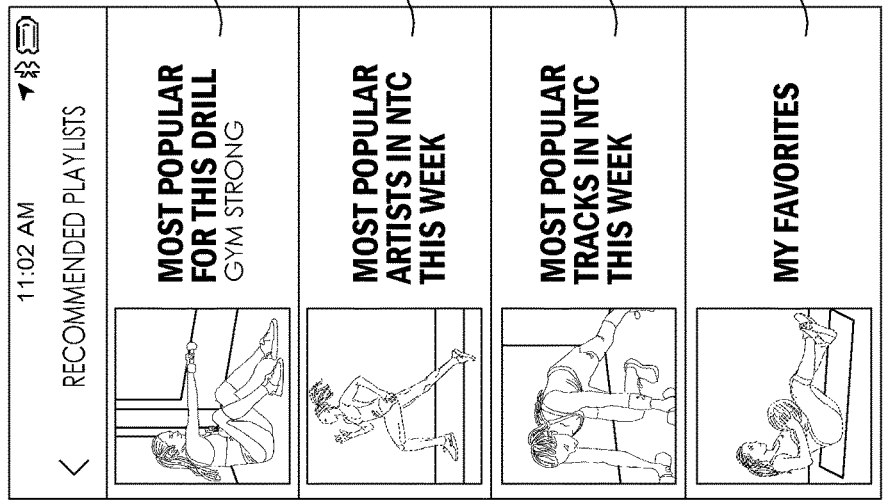
FIG. 18B illustrates an example music playlist selection interface in which options for streaming recommended music playlists are displayed in accordance with example embodiments.
Figure 18A:
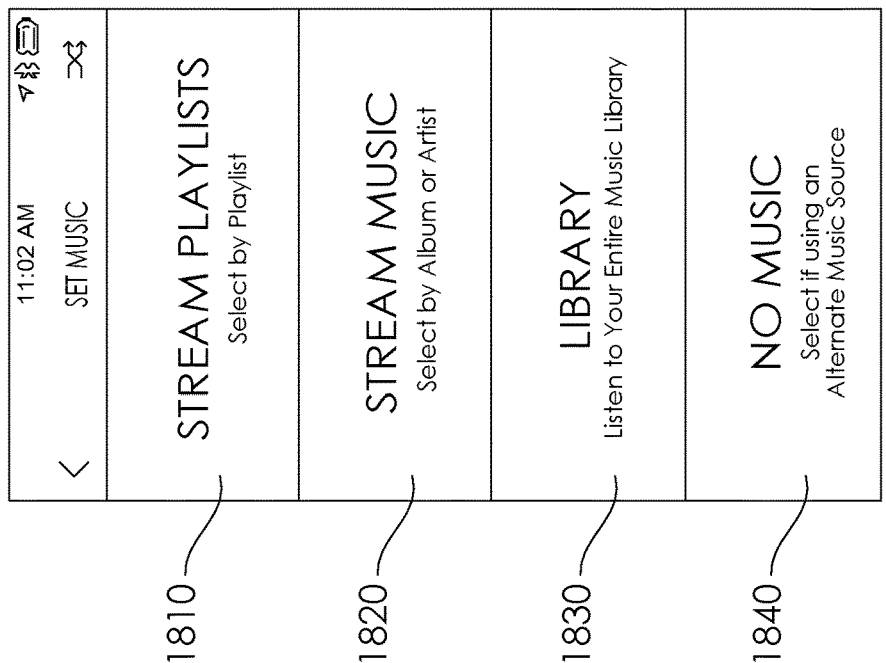
FIG. 18A illustrates an example music setup interface in which options for streaming music and playing music from a library are displayed in accordance with example embodiments.

Station selection menu 965 allows a user to select a music station, e.g., a music genre, from the streaming program for generating a music playlist for an athletic activity. Library music source option 970, on the other hand, may be used to identify a specific source for selecting music. For example, the athlete may indicate that he wishes to have music pulled (i.e., selected) from his or her personal library by selection option 970. The personal library or other music source may be housed in a local database (e.g., a local hard drive) or on a remote network site or both. In one arrangement, a local music library may interface with a workout and music playlist generation system by using application protocols to notify the system of available music in the library. The application protocols may be provided by the workout regimen and playlist generation system to an application managing the music library. FIG. 18A illustrates another embodiment of a music selection interface in which several music setup options are provided, including streaming music from a curated playlist 1810, streaming by a specified artist or song 1820, pulling songs from a music library 1830, and selecting no music 1840.

In another example, an athlete may indicate that he wishes to have music pulled from a particular online music streaming program, e.g., a music streaming program selected from a plurality of music streaming services. The music streaming program option may link the workout program application with a music streaming program application. Thus, the interface 900 may function as a cross-application athletic activity and music streaming program that may include account linking connecting a user's account with the athletic program with an account associated with the music streaming program. In some examples, the user may select an input to access the full music streaming program from the athletic program and switch back and forth between the two programs. The streaming of playlists may be cross-linked with the athletic activity program. In other words, the athletic activity program may provide music content feed when a user selects using the music streaming program, the content feed including curated playlists, music exclusives, most popular artists/playlists/genres for a workout drill/intensity, tempo-based playlists based on a pace or coaching program, and friends' favorites or shares (e.g., by connecting a user's account to friends' accounts within the athletic program and/or by cross-linking accounts of the athletic program with a social media program). By cross-linking a user's account with friends' accounts, the athletic program may also allow a user to view other users' workouts and press a "cheer" button to show that the user has provided a "cheer" for the workout or a "comment" button to provide a text-based comment on the workout.

User song listens, favorites and shares, and/or exclusive tracks may also be captured on display 900 in order to provide additional playlist recommendations. In some examples, the athletic program may have its own curated playlists, e.g., associated with a particular type of athletic activity, available from the music streaming service. The athletic program may create a dynamic workout playlist supported via the music streaming program. For example, a user may provide a playlist genre as a starting point for a playlist of varying intensity based on the athletic program selected. Accordingly, a playlist of music may be generated via the music streaming program which selects a plurality of audio tracks of the specified genre of varying tempos that corresponds to the varying intensities of the workout. The user may also save and/or share the dynamic playlist. Additionally, the athletic program may provide playlist recommendations based on various user parameters, e.g., the selected workout, previously selected playlists, popular playlists, playlists with newly added music, and the like (such as the recommended playlists 1850, 1860, 1870, 1880 shown in the display of FIG. 18B). Information associated with the tempo, tone and/or melody of various audio tracks may be used when generating a playlist corresponding to a selected workout.

As discussed, interface 900 may also include coach selection option 930. In addition or as an alternative to creating a workout similar to the selected coach, coach selection option 930 may also be used to generate a music playlist that is the same as or similar to a playlist the selected coach would use for training For example, the music selection module may identify songs that the selected coach would listen to for generating a training playlist. In some examples, the streaming music program option 975 may identify potential songs that the system believes the user would like based on his or her listening history, frequently played song list, and the like. A frequently played song list may include songs that are most frequently played during workouts (rather than in general). Music may also be recommended based on similarity (as discussed herein), similar purchases, tempo, genre, time period, and country of origin, among other factors. Once the above options for music playlist generation have been configured, the user may select create workout option 945.

According to some embodiments, where a workout music playlist is generated prior to the workout, interface 1000 of FIG. 10 may include a training schedule graph 1035 that illustrates the user's workout. In conjunction with graph 1035, interface 1000 may include a music schedule timeline 1075 that is configured to display the beginning of each song in the playlist. For example, timeline 1075 displays each song as a tick mark 1080 that is aligned with the corresponding portion of the training regimen during which the song will be played. Hovering over or otherwise interacting with one of tick marks 1080 may cause a pop-up window to be generated and displayed. The pop-up window may provide details for the song corresponding to that particular tick mark. In some arrangements, pop-up window may be editable, allowing a user to change the song associated with that tick mark and portion of the training regimen. In some arrangements, the user may "like" or "dislike" a song. Disliking the song may result in replacing the song with another song of similar tempo and/or duration.

Figure 17:
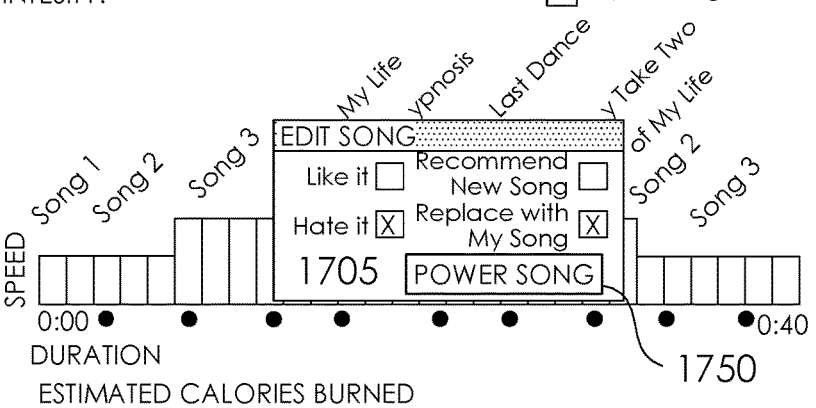
FIG. 17 illustrates an example workout and music playlist generation interface in which a song edit box is displayed for a selected song in accordance with example embodiments.

FIG. 17 illustrates a workout and music playlist generation interface 1700 in which a song edit box 1705 is displayed for a selected song. The user may specify whether the user likes or dislikes the song, whether to recommend a new song for this slot or whether the song should be replaced with a user-selected song. In one or more arrangements, the generation interface 1700 may include an option to replace with a preselected song (or a song from a user's library) and/or a recommend option that asks the system to recommend another song. The recommendation may be based on music or other audio content to which the user has historically performed well (e.g., met or exceeded expectations) or other parameters as discussed herein. In some examples, an additional option 1750 may be provided to play a song in which users have historically performed well, e.g. "power songs," as discussed herein.

The music schedule and the music playlist may also be modified in view of the change in songs. For example, if the new song is shorter than the replaced song, songs that were scheduled to be played after the replaced song may be shifted forward in time to insure that there are no gaps. Alternatively or additionally, other songs in the original playlist may be changed to maximize coverage of the training regimen. That is, songs may be chosen to substantially fill up the duration of the training regimen if the new song modifies duration of the playlist. The playlist generated by the athletic program may also have auto-remix capabilities for certain songs within its music library, e.g., licensed songs. A song may be adjusted on the fly to alter its duration, e.g., by decomposing songs into individual beats, analyzing each beat and matching it to similar sounding beats in the song, and branching different parts of the song together to extend or reduce its duration without a discernible sound that the song has been adjusted.

FIG. 12 illustrates options 1225 and 1230 for defining playlist song selection parameters. The music playlist generation system may use the mood 1225 of the user and the genre of music 1230 to select songs from a music streaming program. If the user is feeling mellow, the system may select slower paced songs. If, on the other hand, the user is feeling upbeat, the system may select faster paced (e.g., more beats per minute) songs. Interface 1200 also allows the user to select a source for the music playlist. For example, a user may select option 1250 to have the playlist generation system pull music from a library and/or option 1255 to have songs pulled from an online music streaming service. In some embodiments, several options corresponding to several online music streaming services may be provided, and a user may select any of the provided music streaming services. Exclusive music content may be provided by the module to certain users based on membership details. Users may also provide recommendations for songs or playlists for motivation and/or specific training programs. Users may also favorite certain songs or playlists and the module may provide favorited songs or playlists to the user in a subsequent workout. Additionally, accounts for the training module and the music streaming program may be linked for compiling user information and preferred songs and playlists.

When an online music streaming program is selected, a plurality of audio tracks may be streamed from the music streaming program during a workout. A playlist of successive audio tracks may be created beforehand based on various input parameters or created on the fly during the workout. The playlist may be created for the athlete to manage his/her pace during the workout, and the playlist may be updated on the fly to, e.g., to inspire with an audio track or higher tempo to increase a pace, or to slow down with a slower temp audio track. During the workout, the training module may receive athletic activity data relating to a performance of the athlete's activity and determine an athletic activity level based on the activity data. The activity data may include at least one of pace, distance, cadence, stride, acceleration, geolocation, and heartrate, and/or may be received from at least one sensor configured to detect movements of the athlete. In some examples, the athletic activity data is transmitted from a wearable device associated with the user, such as capturing device 126 and/or sensor 128.

The athletic activity level may be based on prior athletic activity data received from previous time periods of the workout and/or based on selected workout parameters inputted in the training module 900, e.g., duration 920, speed 925, or intensity 930. In other words, a subsequent desired athletic activity level may be based on prior athletic activity data. For example, a subsequent desired athletic activity level may be determined to be a lower activity level if the workout is nearing the end for a cool down period. If an athlete is in the middle of a long workout, a subsequent athletic activity level may be determined to be high in order to motivate the athlete to continue the workout at a high activity level, e.g., a high speed. Alternatively or additionally, the athlete may input a selection identifying a desired athletic activity level. For example, the training module may include a power boost button, e.g., button 1750 of FIG. 17, that the athlete may press during the workout in order to select a high tempo song or a song that users have rated as a motivating song. In certain implementations, the training module may be configured to motivate the user, regardless of an identified desired athletic activity level received via a user input selection. In some examples, a particular user input selection may identify that the user is not feeling upbeat and/or motivated. The training module may, at a particular time interval of the workout, play a high tempo audio track, regardless of the user's identified desired activity level to motivate the user to run longer or faster.

The training module may accordingly determine a target audio track intensity corresponding to the athletic activity and select a subsequent audio track from the music streaming program that corresponds to the target audio track intensity. In some examples, the target audio track intensity may be based on a target tempo (beats per minute), melody, tone and the like.

Under certain implementations, the training module may accommodate audio advertisements at preset time intervals in between audio tracks from the music streaming program. Accordingly, playing the streamed audio tracks during a workout may be paused, e.g., at a preset time interval and upon completion of an audio track. An advertisement audio track is played and the playing of the streamed audio tracks is subsequently resumed. The timing of the advertisement audio track may also be selected at a preferred point in the workout, e.g., an advertisement is played prior to starting the workout or upon a sensed slowdown or pause in the athletic activity data. Additionally or alternatively, the advertisement audio track may be selected from a plurality of advertisement audio tracks based on the target audio track intensity. For example, if the target audio track intensity is high, the advertisement audio track may be played with a high tempo musical background or an advertisement may be played with a backing track matching the tempo of the ad (e.g., targeted advertising with a beat). In some examples, the advertisement may be selected based on the time period in the workout, e.g., an advertisement including a cheer may be played upon the athlete completing a difficult or high intensity portion of the workout. The advertisement audio track may also be selected based on a geolocation of the athlete during the workout and/or other user information components. For example, if the module has received input that the athletic is female, the workout is running, and the sensed geolocation is the greater New York City area, a selected advertisement audio track may be for the New York City women's marathon.

Referring to FIG. 13, a user may further select a pre-generated workout such as one of workouts 1325. The pre-generated workouts 1325 may have pre-selected/generated playlist associated with the workout regimen. The pre-generated workouts 1325 and corresponding playlists may be generated by other users, celebrity trainers/athletes, and/or coaches and streaming from a music streaming program. The pre-generated workouts 1325 may be retrieved from a database of workouts stored in a network server or may be obtained from a local storage. A user may also select one or more genres 1340 of music that the user wishes to hear during his or her workout. One of genre options 1340 may include a singer/songwriter option that allows a user to pick a particular singer or songwriter rather than or in addition to a genre of music. Alternatively or additionally, a type of coach selected may affect the type of music selected for a workout playlist. For example, if a user selects a taskmaster type 1310a of coach, the music may have faster beats and louder in volume. If a user selects a Zen master (i.e., calmer) type 1310b of coach, the music playlist generation system may select songs that are slower and softer. Further, intensity parameters related to the workout may restrict the coaching playlist to those matching the desired intensity as it varies during the workout.

A selected or generated workout regimen may be displayed immediately in portion 1330 to allow the user to preview the generated workout and music playlist prior to accepting the workout. A user may further modify specific portions of the workout independently of other portions of the workout as described herein. For example, a user may hover over or otherwise interact with a portion of the displayed workout, where upon an edit box (not shown) may appear.

Referring to FIG. 14, a recommended workout summary 1400 may provide identification of segments of the workout in which coaching will be provided. For example, the segments may be labeled with "Coach 1" or other indicators to specify that coaching is scheduled to be provided during that portion of the workout.

FIG. 16 illustrates a proposed pace versus time workout curve 1601 in which various songs in a playlist (as demarcated in music bar 1605) have been selected and mapped to portions of the workout. One method of selecting and mapping songs to the workout may include determining songs that will help motivate or calm the athlete. Thus, for segments of a workout where the athlete is to slow down, a calmer or less motivating song 1603a may be selected and played. Alternatively, for a segment of the workout where the user is to increase his or her pace, a more motivational song such as song 1603b may be played. Songs may also be selected and mapped based on length among other factors. When the workout curve 1601 is mapped against the generated playlist, the user can also more easily determine which songs were playing when performance increased or decreased. For example, a particularly motivating song for the user may have translated to the user significantly increasing the pace of the run. If the user's pace unexpectedly decreased, the user can determine which song was playing and decide if the song factored into the performance wherein the user could revise the playlist omitting such song in future workouts. It is further understood that a user may determine that a particular song(s) translated in the user being able to maintain a constant pace for an extended period of time wherein the workout curve would have a lengthy horizontal segment. Accordingly, incorporating these features of the graphical user interface allows the user to further enhance athletic performance monitoring.

The athletic program may be configured to compile data collected regarding a dynamically-generated playlist and a user's response to the playlist. For example, the program may record if a user fully listened to a song, skipped a song, and/or marked a song as a favorite. By including such user responses to songs in addition to the type and intensity of the workout and the point in time during the workout when the song was played, the athletic program may compile user data and provide better playlists for subsequent workout for the user or for another user with similar input data. Additionally, the athletic program may compile suggested playlists based on a genre, artist, or a random playlist. The athletic program may also compile and suggest trending playlists, curated playlists for particular activities, athlete-curated playlists, friend's playlists, and/or followed playlists.

According to one or more aspects, a user may be given advice regarding whether to change a song. A music selection system may advise against changing a song, for example, if the user has performed favorably during the song in the past. Other reasons for advising against changing a song may include beats per minute being below a certain threshold, genre not being conducive to exercising, length is either too short or too long and the like. The system may also make recommendations for replacement songs. Additionally or alternatively, the user may specifically identify songs that are not to be included. Accordingly, songs may be filtered out of selection contention based on a user's explicit instructions. The user may also specify a genre, era, artist and the like to filter out of a selection database.

A training regimen may also be divided into various phases such as pre-workout or pre-run (e.g., warm up), workout or run and post-workout or post-run (e.g., cool down). Different music playlists may be automatically generated for each of these phases. The music selection for each of these phases may also be different in view of the different purposes of the phases. For example, a pre-run music playlist may include songs that gradually get faster in tempo while a run music playlist may include consistently high beat/tempo songs. A post-run music playlist, on the other hand, may include songs that gradually slow down in tempo to transition the user to a calmer state. Phases and the music selection parameters associated therewith may be automatically defined or manually specified by a user. In one or more examples, a post-run music playlist may be created on the fly at the end of the user's run. The post-run music playlist may be automatically generated based on the songs that appeared to motivate the user more so than other songs. The post-run music playlist may also include live music feeds.

According to one or more aspects, music selection may also be performed based on a separate or integrated GPS device or other location determination system. For example, location information may be used to select a song that is most suited to that location. For example, if a system determines that a user is running in a more rural environment, a slower (e.g., less beats per minute) or softer song may be selected to match the environment. If, on the other hand, the user is running in a city, a more upbeat and/or louder song may be selected. In other arrangements, a song may be selected by determining a user's current or projected elevation. Songs played during previous athletic activity at a similar elevation may then be selected for a current workout or athletic activity, particularly if the user performed at or above a target or expected level (e.g., a pace, a number of calories burned, a distance, etc.). Other song selection parameters may include time of day and speed, both of which may be determined using a GPS or other location determination device.

The created workout and/or associated music playlist may be distributed to various athletic performance devices such as a music player, a workout apparatus such as an elliptical machine or treadmill, a cell phone, laptop computer, desktop computer, home media server and the like. For example, if an athlete is set to begin his or her workout on a treadmill machine, the athlete may upload his or her customized workout to the treadmill to track progress and adherence to the regimen. The data recorded by the treadmill or other workout apparatus or sensor device may further be transmitted to an athletic training site (e.g., a website or database), the athlete's personal music player or other computing device and the like. The information may be stored so that an athlete may review how well they followed the workout regimen and whether they met their goals. The transmission of data may be wired, wireless or any combination thereof. Additionally or alternatively, a music playlist generation system may create a music file by combining multiple music files. The combination of the music files may, in one or more example, include transcoding of the music from one format to another.

Additionally or alternatively, a music selection system may track a user's athletic performance in association with music information. For example, a user's ability to maintain the recommended pace during a running regimen may be tracked based on the music that is being played at the time. Accordingly, the music selection system may be able to identify songs that tend to motivate the athlete to meet or exceed various goals (e.g., expected or estimated workout statistics determined based on user statistics and workout parameters) or athletic performance thresholds. This information may then be used to select songs for future workouts. A training device may record the user's athletic performance in terms of time. The training device or an athletic performance tracking system may then use the athletic performance data to determine times during which the athlete exceeded or met the training regimen's goal and the times at which the athlete did not meet the specified goal. Thus, the athletic performance tracking system may determine that the user met or exceeded the regimen's goals when a first song was playing, but failed to meet the goals when a second song was being played. Accordingly, a music selection system may make note of this fact by specifying a preference for selecting the first song or similar songs over the second song.

Further, an order or sequence of songs selected may also be automatically defined or customized based on various athletic activity or training parameters. For example, if, during a portion of a workout, a user is expected to increase his or her pace over a period of 10 minutes, multiple songs may be selected and ordered such that each subsequent song increases in a number of beats per minute. In another example, if a user is a cool down portion of the workout, the system may select and order songs such that the songs become gradually softer or slower paced.

The data recorded may be displayed as an exercise curve, for example, in which song indicators are shown along the curve. The exercise curve may be displayed on the mobile device or an athletic training site as described above. The athlete may then use the display to identify the songs during which the athlete achieved better performance or where the level of performance declined. The music selection module may then provide song modifications for future workouts.

Conclusion

Embodiments of the invention may simplify the operation of the device and may result in a more compact, power efficient and less complex device. In particular, the selection of audio tracks based on athletic activity may reduce user interaction with the device during the activity. This may enhance battery life. It may also allow the device to employ a simpler user interface, which can further enhance battery life and allow the device to be more compact. Reducing user interaction during an activity may also improve safety by allowing the user to concentrate on the activity and the user's environment.

In any of the above aspects, the various features may be implemented in hardware, or as software modules running on one or more processors. Features of one aspect may be applied to any of the other aspects.

There may also be provided a computer program or a computer program product for carrying out any of the methods described herein, and a computer readable medium having stored thereon a program for carrying out any of the methods described herein. A computer program may be stored on a computer-readable medium, or it could, for example, be in the form of a signal such as a downloadable data signal provided from an Internet website, or it could be in any other form.

While the invention has been described with respect to specific examples including presently preferred modes of carrying out the invention, those skilled in the art will appreciate that there are numerous variations and permutations of the above described systems and methods. For example, various aspects of the invention may be used in different combinations and various different sub-combinations of aspects of the invention may be used, together, in a single system or method without departing from the invention. In one example, software and applications described herein may be embodied as computer readable instructions stored in computer readable media. Also, various elements, components, and/or steps described above may be changed, changed in order, omitted, and/or additional elements, components, and/or steps may be added without departing from this invention. Thus, the invention should be construed broadly.

For the avoidance of doubt, the present application extends to the subject-matter described in the following numbered paragraphs (referred to as "Para" or "Paras"):

1. A method comprising:
   initiating transmission of a stream of audio data comprising a plurality of audio tracks from a music streaming service;
   receiving athletic activity data relating to a performance of an athletic activity by a user during an activity time period, wherein the activity time period includes a plurality of time intervals;
   for each of the plurality of time intervals, determining an athletic activity level from the athletic activity data;
   determining a target audio track intensity corresponding to the athletic activity level; and
   initiating a playback of a streamed audio track corresponding to the target audio track intensity.

2. The method of Para 1, further comprising:
   receiving a user input selection identifying one or more parameters corresponding to an athletic activity program,
   wherein determining the target audio track intensity is based, at least in part, on the athletic activity program.

3. The method of Para 1 or 2, wherein determining a target audio track intensity includes determining a target tempo corresponding to a pace of the athletic activity level.

4. The method of any of the preceding Paras, wherein receiving athletic activity data includes receiving data from at least one sensor configured to detect movements of the user.

5. The method of any of the preceding Paras, wherein the athletic activity data is received from a wearable device associated with the user.

6. The method of any of the preceding Paras, wherein the athletic activity data includes at least one of pace, distance, cadence, stride, acceleration, geolocation, and heartrate.

7. The method of any of the preceding Paras, further comprising:
   receiving a user input selection identifying a desired athletic activity level; and
   selecting a subsequent audio track based on the desired athletic activity level.

8. A method comprising:
   receiving a user input selection identifying a desired athletic activity level for at least one athletic activity to be performed by a user;
   based on the desired athletic activity level, initiating playback of a first streamed audio track from a music streaming service;
   receiving athletic activity data relating to a performance of the athletic activity by the user during a first time period of the athletic activity;
   determining an athletic activity level from the athletic activity data;
   determining a target audio track intensity corresponding to the determined athletic activity level; and
   selecting a second streamed audio track corresponding to the target audio track intensity from the music streaming service regardless of the identified desired athletic activity level of the user input selection.

9. The method of Para 8, wherein the first time period corresponds to a duration of the first streamed audio track.

10. The method of Para 8 or 9, wherein determining a target audio track intensity is based on one of tempo, melody, tone and combinations thereof.

11. The method of any of Paras 8 to 10, wherein receiving athletic activity data includes receiving data from at least one sensor configured to detect movements of a user.

12. The method of any of Paras 8 to 11, wherein the athletic activity data is received from a wearable device associated with the user.

13. A method comprising:
   receiving a user input selection identifying one or more parameters corresponding to an athletic activity program;
   generating an athletic workout for a user based on the user input selection; and
   selecting a plurality of streamed audio tracks from a music streaming service to be played during the athletic workout corresponding to the athletic workout.

14. The method of Para 13, wherein the athletic workout includes a plurality of athletic activity levels and wherein each of the plurality of streamed audio tracks is selected based on a corresponding athletic activity level.

15. The method of Para 13 or 14, wherein the plurality of streamed audio tracks are selected, at least in part, on user account settings associated with the music streaming service.

16. The method of any of Paras 13 to 15, wherein the plurality of streamed audio tracks are selected, at least in part, on a target audio track intensity associated with an athletic activity level during the athletic workout.

17. The method of any of Paras 13 to 16, further comprising:
selecting an advertisement audio track to be played at a selected time interval during the athletic workout;
wherein the selected time interval is based, at least in part, on an amount of completed time of the athletic workout.

18. The method of Para 17, wherein the selected time interval is selected based, at least in part, on sensing a pause or a slowdown of the user during the athletic workout.

19. The method of Para 17 or 18, wherein the advertisement audio track is selected from a plurality of advertisement audio tracks based on a target audio track intensity corresponding to the selected time interval in the athletic workout.

20. The method of any of Paras 17 to 19, wherein the advertisement audio track is selected from a plurality of advertisement audio tracks based on at least one of a geolocation of the user and one or more user information components.

21. A computing device comprising:
a streaming module configured to initiate transmission of a stream of audio data comprising a plurality of audio tracks from a music streaming service;
a training module configured to receive athletic activity data relating to a performance of an athletic activity by a user during an activity time period, wherein the activity time period includes a plurality of time intervals, and, for each of the plurality of time intervals, determine an athletic activity level from the athletic activity data; and
a music selection module configured to determine a target audio track intensity corresponding to the athletic activity level, and to initiate a playback of a streamed audio track corresponding to the target audio track intensity.

22. The computing device of Para 21, wherein the training module is configured to receive a user input selection identifying one or more parameters corresponding to an athletic activity program, and wherein the music selection module determines the target audio track intensity based, at least in part, on the athletic activity program.

23. The computing device of Para 21 or 22, wherein the music selection module determines a target audio track intensity by determining a target tempo corresponding to a pace of the athletic activity level.

24. The computing device of any of Paras 21 to 23, wherein the training module receives data from at least one sensor configured to detect movements of the user.

25. The computing device of any of Paras 21 to 24, wherein the athletic activity data is received from a wearable device associated with the user.

26. The computing device of any of Paras 21 to 25, wherein the athletic activity data includes at least one of pace, distance, cadence, stride, acceleration, geolocation, and heartrate.

27. The computing device of any of Paras 21 to 26, wherein the training module is configured to receive a user input selection identifying a desired athletic activity level; and the music selection module is configured to select a subsequent audio track based on the desired athletic activity level.

28. A computing device comprising:
a user interface configured to receive a user input selection identifying a desired athletic activity level for at least one athletic activity to be performed by a user;
a music selection module configured to initiate playback of a first streamed audio track from a music streaming service based on the desired athletic activity level;
a training module configured to receive athletic activity data relating to a performance of the athletic activity by the user during a first time period of the athletic activity and to determine an athletic activity level from the athletic activity data;
wherein the music selection module is further configured to determine a target audio track intensity corresponding to the determined athletic activity level; and to select a second streamed audio track corresponding to the target audio track intensity from the music streaming service regardless of the identified desired athletic activity level of the user input selection.

29. The computing device of Para 28, wherein the first time period corresponds to a duration of the first streamed audio track.

30. The computing device of Para 28 or 29, wherein the music selection module determines a target audio track intensity based on one of tempo, melody, tone and combinations thereof.

31. The computing device of any of Paras 28 to 30, wherein the training module receives data from at least one sensor configured to detect movements of a user.

32. The computing device of any of Paras 28 to 31, wherein the athletic activity data is received from a wearable device associated with the user.

33. A computing device comprising:
a user interface configured to receive a user input selection identifying one or more parameters corresponding to an athletic activity program;
a training module configured to generate an athletic workout for a user based on the user input selection; and
a music selection module configured to select a plurality of streamed audio tracks from a music streaming service to be played during the athletic workout corresponding to the athletic workout.

34. The computing device of Para 33, wherein the athletic workout includes a plurality of athletic activity levels and wherein each of the plurality of streamed audio tracks is selected based on a corresponding athletic activity level.

35. The computing device of Para 33 or 34, wherein the plurality of streamed audio tracks are selected, at least in part, on user account settings associated with the music streaming service.

36. The computing device of any of Paras 33 to 35, wherein the plurality of streamed audio tracks are selected, at least in part, on a target audio track intensity associated with an athletic activity level during the athletic workout.

37. The computing device of any of Paras 13 to 16, wherein the music selection module is further configured to:
select an advertisement audio track to be played at a selected time interval during the athletic workout;
wherein the selected time interval is based, at least in part, on an amount of completed time of the athletic workout.

38. The computing device of Para 37, wherein the selected time interval is selected based, at least in part, on sensing a pause or a slowdown of the user during the athletic workout.

39. The computing device of Para 37 or 38, wherein the advertisement audio track is selected from a plurality of advertisement audio tracks based on a target audio track intensity corresponding to the selected time interval in the athletic workout.

40. The computing device of any of Paras 37 to 39, wherein the advertisement audio track is selected from a plurality of advertisement audio tracks based on at least one of a geolocation of the user and one or more user information components.

What is claimed is:

1. A method performed by a personal training system comprising:
   receiving, at a processor associated with a user device, a first stream of audio data from a music streaming application, the first stream of audio data including at least a first audio track configured for playback on the user device, wherein the first audio track is selected from the music streaming application based on user settings specific to a type of athletic activity;
   receiving, at the processor, athletic activity data from a sensor of the user device as a user is performing an athletic activity during an activity time period, wherein the activity time period includes at least one time interval corresponding to playback of the first audio track;
   analyzing, at the processor, the received athletic activity data to determine an athletic activity level of the athletic activity data during the at least one time interval;
   determining, at the processor, a target audio track intensity corresponding to an activity time period subsequent to the at least one time interval and based on the athletic activity level during the at least one time interval;
   transmitting, to the music streaming application, the determined target audio track intensity;
   receiving, at the processor, a second stream of audio data from the music streaming application responsive to transmitting the determined target audio track intensity, the second stream of audio data including at least a second audio track configured for playback on the user device, the second audio track corresponding to the target audio track intensity and selected from a plurality of audio tracks in accordance with one or more playback rules of the music streaming application and one or more user preference settings in the music streaming application;
   generating, on a display of the user device, an activity performance display of athletic activity data specific to the playback of the first audio track and the second audio track, the activity performance display including an indication of the target audio track intensity; and
   updating, in the music streaming application, the user settings specific to the type of athletic activity based on the received athletic activity data and the selected second audio track.

2. The method of claim 1, further comprising:
   receiving, at the processor, a user input selection identifying one or more parameters corresponding to the athletic activity,
   wherein determining the target audio track intensity is based, at least in part, on the one or more parameters.

3. The method of claim 1, wherein determining a target audio track intensity includes determining a target tempo corresponding to a pace of the athletic activity level.

4. The method of claim 1, further comprising:
   upon receiving an indication that the user is starting the athletic activity, activating the sensor to detect movements of the user.

5. The method of claim 1, wherein the user device is a wearable device associated with the user.

6. The method of claim 1, wherein the athletic activity data includes at least one of pace, distance, cadence, stride, acceleration, geolocation, and heartrate.

7. The method of claim 1, further comprising:
   receiving, at the processor, a user input selection identifying a desired athletic activity level; and
   receiving, at the processor, a third stream of audio data from the music streaming application, the third stream of audio data including a third audio track configured for playback on the user device, the third audio track corresponding to the desired athletic activity level.

8. A personal training system comprising:
   a sensor configured to measure movement of a user;
   a user device operably connected to the sensor, the user device including a display interface;
   a processor;
   memory storing computer readable instructions that, when executed cause the personal training system to:
      provide, to the display interface of the user device, a cross-application interface comprising an athletic activity application portion and a music streaming application portion;
      receive a user input selection identifying a desired athletic activity level of at least one athletic activity to be performed by the user;
      based on the desired athletic activity level, receive a first stream of audio data from a music streaming application, the first stream of audio data including at least a first audio track configured for playback on the user device, wherein the first audio track is selected from the music streaming application based on user settings specific to a type of athletic activity;
      receive athletic activity data from the sensor during a first time period corresponding to playback of the first audio track as the user performs the athletic activity;
      analyze the received athletic activity data to determine an athletic activity level;
      determine a target audio track intensity corresponding to an activity time period subsequent to the first time period and based on the determined athletic activity level;
      transmit the determined target audio track intensity to the music streaming application;
      receive a second stream of audio data from the music streaming application responsive to transmitting the determined target audio track intensity, the second stream of audio data including at least a second audio track configured for playback on the user device, the second audio track corresponding to the target audio track intensity regardless of the identified desired athletic activity level of the user input selection, wherein the second audio track is selected from a plurality of audio tracks in accordance with one or more playback rules of the music streaming application and one or more user preference settings in the music streaming application;
      generate, on the display interface of the user device, an activity performance display of athletic activity data specific to the playback of the first audio track and the second audio track, the activity performance display including an indication of the target audio track intensity; and update, in the music streaming application, the user settings specific to the type of athletic activity based on the received athletic activity data and the selected second audio track.

9. The personal training system of claim 8, wherein the first time period corresponds to a duration of the first audio track.

10. The personal training system of claim 8, wherein determining a target audio track intensity is based on at least one of: tempo, melody, tone and combinations thereof.

11. The personal training system of claim 8, wherein the sensor is positioned in or on the user device, the user device being a wearable device associated with the user.

12. A method comprising:

receiving, at a processor associated with a user device, a user input selection identifying one or more parameters corresponding to an athletic activity program;

generating, at the processor, an athletic workout for a user based on at least one of: the user input selection or information associated an athletic program account of the user;

receiving, at the processor, a first stream of audio data from a music streaming application, the first stream of audio data including a plurality of streamed audio tracks to be played during the athletic workout, wherein the plurality of streamed audio tracks are selected, at least in part, based on settings associated with a music streaming service account of the user and specific to a type of athletic activity, and one or more parameters associated with the generated athletic workout;

receiving, at the processor, athletic activity data from a sensor of the user device as a user performs the athletic workout during playback of the first stream of audio data;

analyzing, at the processor, the received athletic activity data to determine a target audio track intensity corresponding to the athletic workout during playback of the first stream of audio data;

transmitting, to the music streaming application, the determined target audio track intensity;

receiving, at the processor, a second stream of audio data from the music streaming application responsive to transmitting the determined target audio track intensity, the second stream of audio data including at least a second audio track configured for playback on the user device, the second audio track corresponding to the target audio track intensity and selected from a plurality of audio tracks in accordance with one or more playback rules of the music streaming application and one or more user preference settings in the music streaming application;

generating, on a display of the user device, an activity performance display of the athletic workout, the activity performance display including a plurality of indicators corresponding to time intervals at which each of the plurality of streamed audio tracks are to be played during the athletic workout, and wherein each indicator includes a display of an intensity level of the athletic workout during a respective time interval; and updating, in the music streaming application, the user setting specific to the type of athletic activity based on the received athletic activity data and the selected second audio track.

13. The method of claim 12, wherein the athletic workout includes a plurality of intensity levels and wherein each of the plurality of streamed audio tracks is selected, at least in part, based on a corresponding intensity level.

14. The method of claim 12, wherein the plurality of streamed audio tracks are selected, at least in part, on a target audio track intensity associated with an intensity level during the athletic workout.

15. The method of claim 12, further comprising:

selecting an advertisement audio track to be played at a selected time interval during the athletic workout; and wherein the selected time interval is based, at least in part, on an amount of completed time of the athletic workout.

16. The method of claim 15, wherein the selected time interval is selected based, at least in part, on sensing a pause or a slowdown of the user during the athletic workout.

17. The method of claim 15, wherein the advertisement audio track is selected from a plurality of advertisement audio tracks based on a target audio track intensity corresponding to the selected time interval in the athletic workout.

18. The method of claim 15, wherein the advertisement audio track is selected from a plurality of advertisement audio tracks based on at least one of a geolocation of the user and one or more user information components.

* * * * *